(12) United States Patent
Tomatsu et al.

(10) Patent No.: US 7,972,593 B2
(45) Date of Patent: Jul. 5, 2011

(54) DELIVERY OF THERAPEUTIC AGENTS TO THE BONE

(75) Inventors: Shunji Tomatsu, Saint Louis, MO (US); Adriana Montaño-Suarez, Saint Louis, MO (US); Carlos J. Alméciga-Diaz, Bogoté D.C. (CO); Luis Barrera, Bogoté D.C. (CO)

(73) Assignee: Saint Louis University, Saint Louis, MO (US)

( * ) Notice: Subject to any disclaimer, the term of this patent is extended or adjusted under 35 U.S.C. 154(b) by 0 days.

(21) Appl. No.: 12/497,612

(22) Filed: Jul. 3, 2009

(65) Prior Publication Data

US 2010/0008979 A1     Jan. 14, 2010

Related U.S. Application Data

(60) Provisional application No. 61/081,711, filed on Jul. 17, 2008.

(51) Int. Cl.
   *A01N 63/00* (2006.01)
   *A61K 38/46* (2006.01)
   *C12N 7/00* (2006.01)
   *A61K 38/00* (2006.01)
   *A61K 48/00* (2006.01)

(52) U.S. Cl. .............. 424/93.2; 424/94.6; 435/235.1; 514/1.1; 514/44 R

(58) Field of Classification Search .......... 424/93.2, 424/94.6; 435/235.1; 514/1.1, 44 R
See application file for complete search history.

(56) References Cited

U.S. PATENT DOCUMENTS

| 6,455,495 | B1 | 9/2002 | Orgel et al. |
| 6,491,907 | B1 * | 12/2002 | Rabinowitz et al. ......... 424/93.2 |
| 6,582,692 | B1 | 6/2003 | Podsakoff et al. |
| 2002/0169125 | A1 | 11/2002 | Leung et al. |
| 2006/0014687 | A1 | 1/2006 | Crine et al. |

FOREIGN PATENT DOCUMENTS

| JP | 2852127 | 1/1999 |
| JP | 2000-327583 | 11/2000 |
| JP | 2002-3402 | 1/2002 |
| WO | 95/09611 | 4/1995 |
| WO | 9509611 | 4/1995 |
| WO | 99/33957 | 7/1999 |
| WO | 2005121344 | 12/2005 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Sen et al., Developments in directed evolution for improving enzyme functions. Appl. Biochem. Biotechnol., 2007, vol. 143: 212-223.*
Tomatsu et al., Development of MPS IVA mouse (GaIns(tmhC79S.mC76S)slu) tolerant to human N-acetylgalactosamine-6-sulfate sulfatase. Human Mol. Genetics, 2005, vol. 14 (22): 3321-3335.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Achord et al., Human beta-glucuronidase: in vivo clearance and in vitro uptake by a glycoprotein recognition system on reticuloendothelial cells. Cell 15 (1978) 269-278.
Altarescu, et al., The efficacy of enzyme replacement therapy in patients with chronic neuronopathic Gaucher's disease. J. Pediatr. 138 (2001) 539-547.
Anderson et al., Impaired calcification around matrix vesicles of growth plate and bone in alkaline phosphatase-deficient mice. Am. J. Pathol. 164 (2004) 841-847.
Anderson et al., Matrix vesicles in osteomalacic hypophosphatasia bone contain apatite-like mineral crystals. Am. J. Pathol. 151 (1997) 1555-1561.
Barranger et al., Lessons learned from the development of enzyme therapy for Gaucher disease. J. Inherit. Metab. Dis. 24 (2001) 89-96.
Barton, et al.; Therapeutic response to intravenous infusions of glucocerebrosidase in a patient with Gaucher disease., Proc. Natl. Acad. Sci. USA (1990) 87, 1913-1916.
Barton, et al.; Replacement therapy for inherited enzyme deficiency—macrophage targeted glucocerebrosidase for gaucher's disease., N. Engl. J. Med. (1991) 324, 1464-1470.
Bernardi, "Chromatography of Proteins on Hydroxyapatite", Methods Enzvmol 27:471-9 (1973).
Boskey et al., Matrix vesicles promote mineralization in a gelatin gel. Calcif. Tissue Int. 60 (1997) 309-315.
Boskey, Amorphous calcium phosphate: the contention of bone. J. Dent. Res. 76 (1997) 1433-1436.
Crawley et al., Enzyme replacement therapy in a feline model of Maroteaux-Lamy syndrome. J. Clin. Invest. 97 (1996) 1864-1873.
Dunder, et al.; Enzyme replacement therapy in a mouse model of Aspartylglycosaminuria., FASEB J. (2000)14, 361-367.

(Continued)

*Primary Examiner* — Ganapathirama Raghu
(74) *Attorney, Agent, or Firm* — Randolph Bretton; The Law Office of Randolph Bretton

(57) ABSTRACT

This invention relates to compositions and methods of delivering therapeutic agents to bone. More specifically, the invention relates to endowing a large molecule vectors i.e., adeno virus, retrovirus, liposomes, micelles, natural and synthetic polymers, or combinations thereof, with the ability to target bone tissue in vivo and with improved stability in the blood, by attaching multiple copies of acid amino acid peptides. One preferred embodiment of the invention relates to endowing an adeno-associated virus (AAV) vector with the ability to target bone-tissue in vivo and improve its stability, by the addition of multiple acidic amino acid peptides attached to the capsid of the viral vector.

5 Claims, 9 Drawing Sheets

OTHER PUBLICATIONS

Eng et al., International Collaborative Fabry Disease Study Group, Safety and efficacy of recombinant human alpha galactosidase A-replacement therapy in Fabry's disease. N. Engl. J. Med. 345 (2001) 9-16.

Fujisawa, et al., Acidic amino acid-rich sequences as binding sites of osteonectin to hydroxyapatite crystals. Biochimica et Biophysica Acta (1996) 1292 53-60.

Fujisawa, et al.; Attachment of Osteoblastic Cells to Hydroxyapatite Crystals by a Synthetic Peptide (Glu7-Pro-Arg-Gly-Asp-Thr) Containing two Functional Sequences of Bone Sialoprotein., Matrix Biology vol. (1997) 16/1997, pp. 21-28.

Furbish et al., Uptake and distribution of placental glucocerebrosidase in rat hepatic cells and effects of sequential deglycosylation. Biochim. Biophys. Acta. 673 (1981) 425-434.

Goldberg et al.; Binding of Bone Sialoprotein, Osteopontin and Synthetic Polypeptides to Hydroxyapatite., Connective Tissue Research. (2001) vol. 42(1), pp. 25-37.

Kakkis et al., Enzyme-replacement therapy in mucopolysaccharidosis I. N. Engl. J. Med. 344 (2001) 182-188.

Kasugai, et al., Selective Drug Delivery System to Bone: Small Peptide (Asp)6 Conjugation, (2000) J. Bone. Miner. Res. 15, 936-943.

Kauko, et al: "Type IV Mucopol Ysaccharidosis (Morquio Syndrome), Congenital Metabolic Disorder Syndromes", Japanese Journal of Clinical Medicine, Suppl No. 2, p. 442-445 (1998).

Leone et al., Allosteric modulation of pyrophosphatase activity of rat osseous plate alkaline phosphatase by magnesium ions. Int. J. Biochem. Cell Biol. 30 (1998) 89-97.

Meyer, Can biological calcification occur in the presence of pyrophosphate? Arch. Biochem. Biophys. 15 (1984) 1-8.

Moss et al., Association of inorganic-pyrophosphatase activity with human alkaline-phosphatase preparations. Biochem. J. 102 (1967) 53-57.

Murray, Lectin-specific targeting of lysosomal enzymes to reticuloendothelial cells. Methods Enzymol. 149 (1987) 25-42.

Narisawa et al., Abnormal vitamin B6 metabolism in alkaline phosphatase knock-out mice causes multiple abnormalities, but not the impaired bone mineralization. J Pathol. 191 (2001) 125-133.

Narisawa et al., Inactivation of two mouse alkaline phosphatase genes and establishment of a model of infantile hypophosphatasia. Dev. Dyn. 208 (1997) 432-446.

Nishioka et al., Enhancement of drug delivery to bone: Characterization of human tissue-nonspecific alkaline phosphatase tagged with an acidic oligopeptide. Mol Genet Metab. Jul. 2006; 88(3):244-255. Epub Apr. 17, 2006.

Niwa, et al., "Efficient Selection for High-Expression Transfectants With a Novel Eukaryotic Vector" Gene 108:193-200 (1991).

Roces, et al., Efficacy of enzyme replacement therapy in a-mannosidosis mice: a preclinical animal study. Hum. Mol. Genet. (2004), 13:1979-1988.

Rose. et al: "Primary Structure of the Human Melanoma Associated Antigen p97 (Melanotransferrin) Deduced From the MRNA Sequence" Proc. Natl Acad. Sci. USA. 83:1261-1265 (1986).

Russell et al., Inorganic pyrophosphate in plasma in normal persons and in patients with hypophosphatasia, osteogenesis imperfecta, and other disorders of bone. J. Clin. Invest. 50 (1971) 961-965.

Sands et al., Enzyme replacement therapy for murine mucopolysaccharidosis type VII. J. Clin. Invest. 93 (1994) 2324-2331.

Shull et al., Enzyme replacement in a canine model of Hurler syndrome. Proc. Natl. Acad. Sci. 91 (1994) 12937-12941.

Sly et al., Beta glucuronidase deficiency: Report of clinical, radiologic, and biochemical features of a new mucopolysaccharidosis J Pediatr. (1973) 82:249-257.

Sly, et al., Active site mutant transgene confers tolerance to human b-glucuronidase without affecting the phenotype of MPS VII mice, Proc. Natl. Acad. Sci. USA (2001) 98, 2205-2210.

Stahl et al., Evidence for receptor-mediated binding of glycoproteins, glycoconjugates, and glycosidases by alveolar macrophages. Proc. Natl. Acad. Sci. 75 (1978) 1399-1403.

Tomatsu et al.; Heparan sulfate levels in mucopolysaccharidoses and mucolipidoses J Inherit Metab Dis. (2005). 28:743-57.

Tomatsu et al., Keratan sulphate levels in mucopolysaccharidoses and mucolipidoses J Inherit Metab Dis. (2005) 28:187-202.

Tomatsu, et al, "Morquio Disease: Isolation, Characterization and Expression of Full-Length CDNA for Human N-Acetylgalactosamine-6-Sulfate Sulfatase" Biochem. Biophys. Res. Commun. 181:677-683 (1991).

Vogler et al., Overcoming the blood-brain barrier with high-dose enzyme replacement therapy in murine mucopolysaccharidosis VII Proc Natl Acad Sci USA (2005)102:14777-14782.

Waymire et al., Mice lacking tissue non-specific alkaline phosphatase die from seizures due to defective metabolism of vitamin B-6. Nat. Genet. 11 (1995) 45-51.

Weiss et al., Structure of the Human Liver/Bone/Kidney Alkaline Phasphatase Gene, The Journal of Biological Chemistry, (1988) Vo. 263, No. 24,12002-12010.

Weninger et al., Biochemical and morphological effects of human hepatic alkaline phosphatase in a neonate with hypophosphatasia. Acta Paediatr. Scand. Suppl. 360 (1989) 154-160.

Whyte et al., Alkaline phosphatase: placental and tissue-nonspecific isoenzymes hydrolyze phosphoethanolamine, inorganic pyrophosphatem and pyridoxal 5'-phosphate. Substrate accumulation in carriers of hypophosphatasia corrects during pregnancy. J. Clin. Invest. 95 (1995) 1440-1445.

Whyte et al., Enzyme replacement therapy for infantile hypophosphatasia attempted by intravenous infusions of alkaline phosphatase-rich Paget plasma: results in three additional patients. J. Pediatr. 105 (1984) 926-933.

Whyte et al., Infantile hypophosphatasia: enzyme replacement therapy by intravenous infusion of alkaline phosphatase-rich plasma from patients with Paget bone disease. J. Pediatr. 101 (1982) 379-386.

Whyte et al., Infantile hypophosphatasia: normalization of circulating bone alkaline phosphatase activity followed byskeletal remineralization. Evidence for an intact structural gene for tissue nonspecific alkaline phosphatase. J. Pediatr. D 108 (1986) 82-88.

Whyte, et al., Hypophosphatasia and the Role of Alkaline Phosphatase in Skeletal Mineralization, Endocrine Reviews, (1994), vol. 15, No. 4, 439-461.

Yokogawa et al., Selective Delivery of Estradiol to Bone by Aspartic Acid Oligopeptide and Its Effects on Ovariectomized Mice, (2001) Endocrinology 142,1228-1233.

Buning, et al. Receptor targeting of adeno-associated virus vectors, Gene Ther 10: 1142-1151, (2003).

Choi et al. AAV Hybrid Serotypes: Improved Vectors for Gene Delivery, Curr Gen Ther 5: 299-310, (2005).

Flotte, Gene Therapy Progress and Prospects: Recombinant adeno-associated virus (rAAV) vectors Gene Ther 11: 805-810, (2004).

Gittens et al. Designing proteins for bone targeting Adv Drug Deliv Rev. 57: 1011-1036, (2005).

Nam et al., Structure of Adeno-Associated Virus Serotype 8, a Gene Therapy Vector J Virol 81: 12260-12271, (2007).

Niwa et al., Efficient selection for high-expression transfectants with a novel eukaryotic vector, Dec. 15;108(2):193-200, (1991).

Shi et al., Insertional Mutagenesis of the Adena-Associated Virus Type 2 (AAV2) Capsid Gene and Generation of AAV2 Vectors Targeted to Alternative Cell-Surface Receptors. Hum Gene Ther 12: 1697-1711, (2001).

Wu et al. Mutational Analysis of the Adeno-Associated Virus Type 2 (AAV2) Capsid Gene and Construction of AAV2 Vectors with Altered Tropism. J Virol 74: 8635-8647, (2000).

Xiao et al. Production of high-titer recombinant adeno-associated virus vectors in the absence of helper adenovirus. J Virol 72: 2224-2232, (1998).

Xie et al. The atomic structure of adeno-associated virus (AAV-2), a vector for human gene therapy, Proc Natl Acad Sci USA 99: 10405-10410, (2002).

Zolotukhin et al. Recombinant adeno-associated virus purification using novel methods improves infectious titer and yield, Gene Ther 6: 973-985, (1999).

* cited by examiner

SEQUENCE LISTING

<160> NUMBER OF SEQ ID NOS: 8

<210> SEQ ID NO 1
<211> LENGTH: 8332
<212> TYPE: DNA
<213> ORGANISM: adeno-associated virus 2

<400> SEQUENCE: 1

| | | | | | |
|---|---|---|---|---|---:|
| cgcctctccc | cgcgcgttgg | ccgattcatt | aatgcagaat | tcccatcatc | aataatatac | 60 |
| cttattttgg | attgaagcca | atatgataat | gaggggggtgg | agtttgtgac | gtggcgcggg | 120 |
| gcgtgggaac | ggggcgggtg | acgtagtagc | tctagaggtc | ctgtattaga | ggtcacgtga | 180 |
| gtgttttgcg | acattttgcg | acaccatgtg | gtcacgctgg | gtatttaagc | ccgagtgagc | 240 |
| acgcagggtc | tccattttga | agcgggaggt | ttgaacgcgc | agccaccacg | gcggggtttt | 300 |
| acgagattgt | gattaaggtc | cccagcgacc | ttgacgagca | tctgcccggc | atttctgaca | 360 |
| gctttgtgaa | ctgggtggcc | gagaaggaat | gggagttgcc | gccagattct | gacatggatc | 420 |
| tgaatctgat | tgagcaggca | cccctgaccg | tggccgagaa | gctgcagcgc | gactttctga | 480 |
| cggaatggcg | ccgtgtgagt | aaggcccccgg | aggcccttttt | ctttgtgcaa | tttgagaagg | 540 |
| gagagagcta | cttccacatg | cacgtgctcg | tggaaaccac | cggggtgaaa | tccatggttt | 600 |
| tgggacgttt | cctgagtcag | attcgcgaaa | aactgattca | gagaatttac | cgcgggatcg | 660 |
| agccgacttt | gccaaactgg | ttcgcggtca | caaagaccag | aaatggcgcc | ggaggcggga | 720 |
| acaaggtggt | ggatgagtgc | tacatcccca | attacttgct | ccccaaaaacc | cagcctgagc | 780 |
| tccagtgggc | gtggactaat | atggaacagt | atttaagcgc | ctgtttgaat | ctcacggagc | 840 |
| gtaaacggtt | ggtggcgcag | catctgacgc | acgtgtcgca | gacgcaggag | cagaacaaag | 900 |
| agaatcagaa | tcccaattct | gatgcgccgg | tgatcagatc | aaaaacttca | gccaggtaca | 960 |
| tggagctggt | cgggtggctc | gtggacaagg | ggattacctc | ggagaagcag | tggatccagg | 1020 |
| aggaccaggc | ctcatacatc | tccttcaatg | cggcctccaa | ctcgcggtcc | caaatcaagg | 1080 |
| ctgccttgga | caatgcggga | aagattatga | gcctgactaa | aaccgccccc | gactacctgg | 1140 |
| tgggccagca | gcccgtggag | gacatttcca | gcaatcggat | ttataaaatt | ttggaactaa | 1200 |
| acgggtacga | tccccaatat | gcggcttccg | tctttctggg | atgggccacg | aaaaagttcg | 1260 |
| gcaagaggaa | caccatctgg | ctgtttgggc | ctgcaactac | cgggaagacc | aacatcgcgg | 1320 |
| aggccatagc | ccacactgtg | cccttctacg | ggtgcgtaaa | ctggaccaat | gagaactttc | 1380 |
| ccttcaacga | ctgtgtcgac | aagatggtga | tctggtggga | ggagggggaag | atgaccgcca | 1440 |
| aggtcgtgga | gtcggccaaa | gccattctcg | gaggaagcaa | ggtgcgcgtg | gaccagaaat | 1500 |
| gcaagtcctc | ggcccagata | gacccgactc | ccgtgatcgt | cacctccaac | accaacatgt | 1560 |
| gcgccgtgat | tgacgggaac | tcaacgacct | tcgaacacca | gcagccgttg | caagaccgga | 1620 |
| tgttcaaatt | tgaactcacc | cgccgtctgg | atcatgactt | tgggaaggtc | accaagcagg | 1680 |
| aagtcaaaga | cttttttcgg | tgggcaaagg | atcacgtggt | tgaggtggag | catgaattct | 1740 |
| acgtcaaaaa | gggtggagcc | aagaaaagac | ccgccccccag | tgacgcagat | ataagtgagc | 1800 |
| ccaaacgggt | gcgcgagtca | gttgcgcagc | catcgacgtc | agacgcggaa | gcttcgatca | 1860 |
| actacgcaga | caggtaccaa | aacaaatgtt | ctcgtcacgt | gggcatgaat | ctgatgctgt | 1920 |
| ttccctgcag | acaatgcgag | agaatgaatc | agaattcaaa | tatctgcttc | actcacggac | 1980 |
| agaaagactg | tttagagtgc | tttcccgtgt | cagaatctca | acccgttttct | gtcgtcaaaa | 2040 |

-continued

```
aggcgtatca gaaactgtgc tacattcatc atatcatggg aaaggtgcca gacgcttgca       2100
ctgcctgcga tctggtcaat gtggatttgg atgactgcat cttttgaacaa taaatgattt      2160 aaatcaggta tggctgccga tggttatctt ccagattggc tcgaggacac tctctctgaa       2220
ggaataagac agtggtggaa gctcaaacct ggcccaccac caccaaagcc cgcagagcgg       2280
cataaggacg acagcagggg tcttgtgctt cctgggtaca agtacctcgg acccttcaac      2340
ggactcgaca agggagagcc ggtcaacgag gcagacgccg cggccctcga gcacgacaaa      2400
gcctacgacc ggcagctcga cagcggagac aacccgtacc tcaagtacaa ccacgccgac      2460
gcggagtttc aggagcgcct taaagaagat acgtcttttg ggggcaacct cggacgagca      2520
gtcttccagg cgaaaaagag ggttcttgaa cctctgggcc tggttgagga acctgttaag      2580
acggctccgg gaaaaagag gccggtagag cactctcctg tggagccaga ctcctcctcg      2640
ggaaccggaa aggcgggcca gcagcctgca agaaaaagat tgaattttgg tcagactgga      2700
gacgcagact cagtacctga cccccagcct ctcggacagc caccagcagc ccctctggt      2760 ctgggaacta atacgatggc tacaggcagt ggcgcaccaa tggcagacaa taacgagggc      2820
gccgacggag tgggtaattc ctcgggaaat tggcattgcg attccacatg gatgggcgac      2880
agagtcatca ccaccagcac ccgaacctgg gccctgccca cctacaacaa ccacctctac      2940
aaacaaattt ccagccaatc aggagcctcg aacgacaatc actactttgg ctacagcacc      3000 ccttggggt attttgactt caacagattc cactgccact tttcaccacg tgactggcaa       3060
agactcatca caacaactg gggattccga cccaagagac tcaacttcaa gctctttaac      3120
attcaagtca aagaggtcac gcagaatgac ggtacgacga cgattgccaa taaccttacc      3180
agcacggttc agtgtttac tgactcgag taccagctcc cgtacgtcct cggctcggcg        3240
catcaaggat gcctcccgcc gttcccagca gacgtcttca tggtgccaca gtatggatac      3300 ctcacctga caacgggag tcaggcagta ggacgctctt catttactg cctggagtac         3360 tttccttctc agatgctgcg taccggaaac aactttacct tcagctacac tttgaggac      3420 gttccttttcc acagcagcta cgctcacagc cagagtctgg accgtctcat gaatcctctc     3480
atcgaccagt acctgtatta cttgagcaga acaaacactc caagtggaac caccacgcag     3540
tcaaggcttc agtttctca ggccggagcg agtgacattc gggaccagtc taggaactgg      3600
cttcctggac cctgttaccg ccagcagcga gtatcaaaga catctgcgga taacaacaac      3660
agtgaatact cgtggactgg agctaccaag taccacctca atggcagaga ctctctggtg      3720
aatccgggcc cggccatggc aagccacaag gacgatgaag aaaagttttt tcctcagagc     3780
ggggttctca tctttgggaa gcaaggctca gagaaacaa atgtggacat tgaaaaggtc      3840
atgattacag acgaagagga aatcaggaca accaatcccg tggctacgga gcagtatggt     3900
tctgtatcta ccaacctcca gagaggcaac agacaagcag ctaccgcaga tgtcaacaca      3960
caaggcgttc ttccaggcat ggtctggcag gacagagatg tgtaccttca ggggcccatc     4020
tgggcaaaga ttccacacac ggacggacat tttcacccct ctccctcat gggtggattc      4080 ggacttaaac accctcctcc acagattctc atcaagaaca cccggtacc tgcgaatcct      4140 tcgaccacct tcagtgcggc aaagtttgct tccttcatca cacagtactc cacgggacag     4200
gtcagcgtgg agatcgagtg ggagctgcag aaggaaaaca gcaaacgctg gaatcccgaa     4260
attcagtaca cttccaacta caacaagtct gttaatgtgg actttactgt ggacactaat     4320
ggcgtgtatt cagagcctcg cccattggc accagatacc tgactcgtaa tctgtaattg      4380
cttgttaatc aataaaccgt ttaattcgtt tcagttgaac tttggtctct gcgtatttct      4440
```

```
ttcttatcta gtttccatgc tctagaggtc ctgtattaga ggtcacgtga gtgttttgcg    4500
acattttgcg acaccatgtg gtcacgctgg gtatttaagc ccgagtgagc acgcagggtc    4560
tccattttga agcgggaggt ttgaacgcgc agccaccacg gcggggtttt acgagattgt    4620
gattaaggtc cccagcgacc ttgacgagca tctgcccggc atttctgaca gctttgtgaa    4680
ctgggtggcc gagaaggaat gggagttgcc gccagattct gacatggatc tgaatctgat    4740
tgagcaggca cccctgaccg tggccgagaa gctgcatcgc tggcgtaata gcgaagaggc    4800
ccgcaccgat cgcccttccc aacagttgcg cagcctgaat ggcgaatggc gattccgttg    4860
caatggctgg cggtaatatt gttctggata ttaccagcaa ggccgatagt ttgagttctt    4920
ctactcaggc aagtgatgtt attactaatc aaagaagtat tgcgacaacg gttaatttgc    4980
gtgatggaca gactctttta ctcggtggcc tcactgatta aaaaacact tctcaggatt    5040
ctggcgtacc gttcctgtct aaaatccctt taatcggcct cctgtttagc tcccgctctg    5100
attctaacga ggaaagcacg ttatacgtgc tcgtcaaagc aaccatagta cgcgccctgt    5160
agcggcgcat taagcgcggc gggtgtggtg gttacgcgca gcgtgaccgc tacacttgcc    5220
agcgccctag cgcccgctcc tttcgctttc ttcccttcct ttctcgccac gttcgccggc    5280
tttccccgtc aagctctaaa tcgggggctc cctttagggt tccgatttag tgctttacgg    5340
cacctcgacc ccaaaaaact tgattagggt gatggttcac gtagtgggcc atcgccctga    5400
tagacggttt ttcgcccttt gacgttggag tccacgttct ttaatagtgg actcttgttc    5460
caaactggaa caacactcaa ccctatctcg gtctattctt ttgatttata agggattttg    5520
ccgatttcgg cctattggtt aaaaaatgag ctgatttaac aaaaatttaa cgcgaatttt    5580
aacaaaatat taacgtttac aatttaaata tttgcttata caatcttcct gttttttgggg    5640
cttttctgat tatcaaccgg ggtacatatg attgacatgc tagttttacg attaccgttc    5700
atcgattctc ttgtttgctc cagactctca ggcaatgacc tgatagcctt tgtagagacc    5760
tctcaaaaat agctaccctc tccggcatga atttatcagc tagaacggtt gaatatcata    5820
ttgatggtga tttgactgtc tccggccttt ctcacccgtt tgaatcttta cctacacatt    5880
actcaggcat tgcatttaaa atatatgagg gttctaaaaa ttttttatcct tgcgttgaaa    5940
taaaggcttc tcccgcaaaa gtattacagg gtcataatgt ttttggtaca accgatttag    6000
ctttatgctc tgaggcttta ttgcttaatt ttgctaattc tttgccttgc ctgtatgatt    6060
tattggatgt tgcaattcct gatgcggtat tttctcctta cgcatctgtg cggtatttca    6120
caccgcatat ggtgcactct cagtacaatc tgctctgatg ccgcatagtt aagccagccc    6180
cgacacccgc caacacccgc tgacgcgccc tgacgggctt gtctgctccc ggcatccgct    6240
tacagacaag ctgtgaccgt ctccgggagc tgcatgtgtc agaggttttc accgtcatca    6300
ccgaaacgcg cgagacgaaa gggcctcgtg atacgcctat ttttataggt taatgtcatg    6360
ataataatgg tttcttagac gtcaggtggc acttttcggg gaaatgtgcg cggaacccct    6420
atttgtttat ttttctaaat acattcaaat atgtatccgc tcatgagaca ataaccctga    6480
taaatgcttc aataatattg aaaaaggaag agtatgagta ttcaacattt ccgtgtcgcc    6540
cttattccct ttttttgcggc attttgcctt cctgtttttg ctcacccaga aacgctggtg    6600
aaagtaaaag atgctgaaga tcagttgggt gcacgagtgg gttacatcga actggatctc    6660
aacagcggta agatccttga gagttttcgc cccgaagaac gttttccaat gatgagcact    6720
tttaaagttc tgctatgtgg cgcggtatta tcccgtattg acgccgggca agagcaactc    6780
ggtcgccgca tacactattc tcagaatgac ttggttgagt actcaccagt cacagaaaag    6840
```

| | |
|---|---|
| catcttacgg atggcatgac agtaagagaa ttatgcagtg ctgccataac catgagtgat | 6900 |
| aacactgcgg ccaacttact tctgacaacg atcggaggac cgaaggagct aaccgctttt | 6960 |
| ttgcacaaca tgggggatca tgtaactcgc cttgatcgtt gggaaccgga gctgaatgaa | 7020 |
| gccataccaa acgacgagcg tgacaccacg atgcctgtag caatggcaac aacgttgcgc | 7080 |
| aaactattaa ctggcgaact acttactcta gcttcccggc aacaattaat agactggatg | 7140 |
| gaggcggata aagttgcagg accacttctg cgctcggccc ttccggctgg ctggtttatt | 7200 |
| gctgataaat ctggagccgg tgagcgtggg tctcgcggta tcattgcagc actggggcca | 7260 |
| gatggtaagc cctcccgtat cgtagttatc tacacgacgg ggagtcaggc aactatggat | 7320 |
| gaacgaaata gacagatcgc tgagataggt gcctcactga ttaagcattg gtaactgtca | 7380 |
| gaccaagttt actcatatat actttagatt gatttaaaac ttcattttta atttaaaagg | 7440 |
| atctaggtga agatcctttt tgataatctc atgaccaaaa tcccttaacg tgagttttcg | 7500 |
| ttccactgag cgtcagaccc cgtagaaaag atcaaaggat cttcttgaga tcctttttttt | 7560 |
| ctgcgcgtaa tctgctgctt gcaaacaaaa aaaccaccgc taccagcggt ggtttgtttg | 7620 |
| ccggatcaag agctaccaac tctttttccg aaggtaactg gcttcagcag agcgcagata | 7680 |
| ccaaatactg tccttctagt gtagccgtag ttaggccacc acttcaagaa ctctgtagca | 7740 |
| ccgcctacat acctcgctct gctaatcctg ttaccagtgg ctgctgccag tggcgataag | 7800 |
| tcgtgtctta ccgggttgga ctcaagacga tagttaccgg ataaggcgca gcggtcgggc | 7860 |
| tgaacggggg gttcgtgcac acagcccagc ttggagcgaa cgacctacac cgaactgaga | 7920 |
| tacctacagc gtgagctatg agaaagcgcc acgcttcccg aagggagaaa ggcggacagg | 7980 |
| tatccggtaa gcggcagggt cggaacagga gagcgcacga gggagcttcc agggggaaac | 8040 |
| gcctggtatc tttatagtcc tgtcgggttt cgccacctct gacttgagcg tcgatttttg | 8100 |
| tgatgctcgt caggggggcg gagcctatgg aaaaacgcca gcaacgcggc ctttttacgg | 8160 |
| ttcctggcct tttgctggcc ttttgctcac atgttctttc ctgcgttatc ccctgattct | 8220 |
| gtggataacc gtattaccgc ctttgagtga gctgataccg ctcgccgcag ccgaacgacc | 8280 |
| gagcgcagcg agtcagtgag cgaggaagcg gaagagcgcc caatacgcaa ac | 8332 |

<210> SEQ ID NO 2
<211> LENGTH: 8356
<212> TYPE: DNA
<213> ORGANISM: adeno-associated virus 2

<400> SEQUENCE: 2

| | |
|---|---|
| cgcctctccc cgcgcgttgg ccgattcatt aatgcagaat tcccatcatc aataatatac | 60 |
| cttattttgg attgaagcca atatgataat gaggggggtgg agtttgtgac gtggcgcggg | 120 |
| gcgtgggaac ggggcgggtg acgtagtagc tctagaggtc ctgtattaga ggtcacgtga | 180 |
| gtgttttgcg acattttgcg acaccatgtg gtcacgctgg gtatttaagc ccagtgagc | 240 |
| acgcagggtc tccattttga agcgggaggt ttgaacgcgc agccaccacg gcgggttt | 300 |
| acgagattgt gattaaggtc cccagcgacc ttgacgagca tctgcccggc atttctgaca | 360 |
| gctttgtgaa ctgggtggcc gagaaggaat gggagttgcc gccagattct gacatggatc | 420 |
| tgaatctgat tgagcaggca cccctgaccg tggccgagaa gctgcagcgc gactttctga | 480 |
| cggaatggcg ccgtgtgagt aaggcccgg aggccctttt ctttgtgcaa tttgagaagg | 540 |
| gagagagcta cttccacatg cacgtgctcg tggaaaccac cggggtgaaa tccatggttt | 600 |
| tgggacgttt cctgagtcag attcgcgaaa aactgattca gagaatttac cgcgggatcg | 660 |

```
agccgacttt gccaaactgg ttcgcggtca caaagaccag aaatggcgcc ggaggcggga    720
acaaggtggt ggatgagtgc tacatcccca attacttgct ccccaaaacc cagcctgagc    780
tccagtgggc gtggactaat atggaacagt atttaagcgc ctgtttgaat ctcacggagc    840
gtaaacggtt ggtggcgcag catctgacgc acgtgtcgca gacgcaggag cagaacaaag    900
agaatcagaa tcccaattct gatgcgccgg tgatcagatc aaaaacttca gccaggtaca    960
tggagctggt cgggtggctc gtggacaagg ggattacctc ggagaagcag tggatccagg   1020
aggaccaggc ctcatacatc tccttcaatg cggcctccaa ctcgcggtcc caaatcaagg   1080
ctgccttgga caatgcggga aagattatga gcctgactaa aaccgccccc gactacctgg   1140
tgggccagca gcccgtggag gacatttcca gcaatcggat ttataaaatt ttggaactaa   1200
acgggtacga tccccaatat gcggcttccg tctttctggg atgggccacg aaaaagttcg   1260
gcaagaggaa caccatctgg ctgtttgggc ctgcaactac cgggaagacc aacatcgcgg   1320
aggccatagc ccacactgtg cccttctacg ggtgcgtaaa ctggaccaat gagaactttc   1380
ccttcaacga ctgtgtcgac aagatggtga tctggtggga ggaggggaag atgaccgcca   1440
aggtcgtgga gtcggccaaa gccattctcg gaggaagcaa ggtgcgcgtg gaccagaaat   1500
gcaagtcctc ggcccagata gacccgactc ccgtgatcgt cacctccaac accaacatgt   1560
gcgccgtgat tgacgggaac tcaacgacct tcgaacacca gcagccgttg caagaccgga   1620
tgttcaaatt tgaactcacc cgccgtctgg atcatgactt tgggaaggtc accaagcagg   1680
aagtcaaaga cttttttccgg tgggcaaagg atcacgtggt tgaggtggag catgaattct   1740
acgtcaaaaa gggtggagcc aagaaaagac ccgcccccag tgacgcagat ataagtgagc   1800
ccaaacgggt gcgcgagtca gttgcgcagc catcgacgtc agacgcggaa gcttcgatca   1860
actacgcaga caggtaccaa aacaaatgtt ctcgtcacgt gggcatgaat ctgatgctgt   1920
ttccctgcag acaatgcgag agaatgaatc agaattcaaa tatctgcttc actcacggac   1980
agaaagactg tttagagtgc tttcccgtgt cagaatctca acccgtttct gtcgtcaaaa   2040
aggcgtatca gaaactgtgc tacattcatc atatcatggg aaaggtgcca gacgcttgca   2100
ctgcctgcga tctggtcaat gtggatttgg atgactgcat ctttgaacaa taatgatttt   2160
aaatcaggta tggctgccga tggttatctt ccagattggc tcgaggacac tctctctgaa   2220
ggaataagac agtggtggaa gctcaaacct ggcccaccac caccaaagcc cgcagagcgg   2280
cataaggacg acagcagggg tcttgtgctt cctgggtaca agtacctcgg acccttcaac   2340
ggactcgaca agggagagcc ggtcaacgag gcagacgccg cggcccctcga gcacgacaaa   2400 gcctacgacc ggcagctcga cagcggagac aacccgtacc tcaagtacaa ccacgccgac   2460
gcggagtttc aggagcgcct taagaagat acgtcttttg ggggcaacct cggacgagca   2520
gtcttccagg cgaaaaagag ggttcttgaa cctctgggcc tggttgagga acctgttaag   2580
acggatgatg atgatgatga tgacgacgct ccgggaaaaa agaggccggt agagcactct   2640
cctgtggagc cagactcctc ctcgggaacc ggaaaggcgg gccagcagcc tgcaagaaaa   2700
agattgaatt ttggtcagac tggagacgca gactcagtac ctgaccccca gcctctcgga   2760
cagccaccag cagcccctc tggtctggga actaatacga tggctacagg cagtggcgca   2820 ccaatgcag acaataacga gggcgccgac ggagtgggta attcctcggg aaattggcat   2880
tgcgattcca catggatggg cgacagagtc atcaccacca gcacccgaac ctgggccctg   2940
cccacctaca caaccaccct ctacaaacaa atttccagcc aatcaggagc ctcgaacgac   3000
aatcactact ttggctacag caccccttgg gggtattttg acttcaacag attccactgc   3060
```

```
cacttttcac cacgtgactg gcaaagactc atcaacaaca actggggatt ccgacccaag    3120
agactcaact tcaagctctt taacattcaa gtcaaagagg tcacgcagaa tgacggtacg    3180
acgacgattg ccaataacct taccagcacg gttcaggtgt ttactgactc ggagtaccag    3240
ctcccgtacg tcctcggctc ggcgcatcaa ggatgcctcc cgccgttccc agcagacgtc    3300
ttcatggtgc cacagtatgg atacctcacc ctgaacaacg ggagtcaggc agtaggacgc    3360
tcttcatttt actgcctgga gtactttcct tctcagatgc tgcgtaccgg aaacaacttt    3420
accttcagct cacttttga ggacgttcct ttccacagca gctacgctca cagccagagt    3480
ctggaccgtc tcatgaatcc tctcatcgac cagtacctgt attacttgag cagaacaaac    3540
actccaagtg gaaccaccac gcagtcaagg cttcagtttt ctcaggccgg agcgagtgac    3600
attcgggacc agtctaggaa ctggcttcct ggaccctgtt accgccagca gcagtatca    3660 aagacatctg cggataacaa caacagtgaa tactcgtgga ctggagctac caagtaccac    3720
ctcaatggca gagactctct ggtgaatccg ggcccggcca tggcaagcca aggacgat    3780 gaagaaaagt ttttcctca gagcggggtt ctcatctttg ggaagcaagg ctcagagaaa    3840
acaaatgtgg acattgaaaa ggtcatgatt acagacgaag aggaaatcag acaaccaat    3900 cccgtggcta cggagcagta tggttctgta tctaccaacc tccagagagg caacagacaa    3960
gcagctaccg cagatgtcaa cacacaaggc gttcttccag gcatggtctg gcaggacaga    4020
gatgtgtacc ttcaggggcc catctgggca aagattccac acacggacgg acattttcac    4080
ccctctcccc tcatgggtgg attcggactt aaacaccctc ctccacagat tctcatcaag    4140
aacaccccgg tacctgcgaa tccttcgacc accttcagtg cggcaaagtt tgcttccttc    4200
atcacacagt actccacggg acaggtcagc gtggagatcg agtgggagct gcagaaggaa    4260
aacagcaaac gctggaatcc cgaaattcag tacacttcca actacaacaa gtctgttaat    4320
gtggacttta ctgtgacac taatggcgtg tattcagagc ctcgcccat ggcaccaga    4380 tacctgactc gtaatctgta attgcttgtt aatcaataaa ccgtttaatt cgtttcagtt    4440
gaactttggt tctgtgcgtat ttcttctta tctagttttcc atgctctaga ggtcctgtat    4500
tagaggtcac gtgagtgttt tgcgacattt tgcgacacca tgtggtcacg ctgggtattt    4560
aagcccgagt gagcacgcag ggtctccatt ttgaagcggg aggtttgaac gcgcagccac    4620
cacggcgggg ttttacgaga ttgtgattaa ggtccccagc gaccttgacg agcatctgcc    4680
cggcatttct gacagctttg tgaactgggt ggccgagaag gaatgggagt gccgccaga    4740 ttctgacatg gatctgaatc tgattgagca ggcacccctg accgtggccg agaagctgca    4800
tcgctggcgt aatagcgaag aggcccgcac cgatcgccct tcccaacagt tgcgcagcct    4860
gaatggcgaa tggcgattcc gttgcaatgg ctggcgtaa tattgttctg gatattacca    4920
gcaaggccga tagtttgagt tcttctactc aggcaagtga tgttattact aatcaaagaa    4980
gtattgcgac aacggttaat ttgcgtgatg acagactct tttactcggt ggcctcactg    5040
attataaaaa cacttctcag gattctggcg taccgttcct gtctaaaatc cctttaatcg    5100
gcctcctgtt tagctcccgc tctgattcta acgaggaaag cacgttatac gtgctcgtca    5160
aagcaaccat agtacgcgcc ctgtagcggc gcattaagcg cggcgggtgt ggtggttacg    5220
cgcagcgtga ccgctacact tgccagcgcc ctagcgcccg ctcctttcgc tttcttccct    5280
tcctttctcg ccacgttcgc cggctttccc cgtcaagctc taaatcgggg gctcccttta    5340
gggttccgat ttagtgcttt acggcacctc gaccccaaaa aacttgatta gggtgatggt    5400
tcacgtagtg ggccatcgcc ctgatagacg gttttttcgcc ctttgacgtt ggagtccacg    5460
```

```
ttctttaata gtggactctt gttccaaact ggaacaacac tcaaccctat ctcggtctat    5520
tcttttgatt tataagggat tttgccgatt tcggcctatt ggttaaaaaa tgagctgatt    5580
taacaaaaat ttaacgcgaa ttttaacaaa atattaacgt ttacaattta aatatttgct    5640
tatacaatct tcctgttttt ggggcttttc tgattatcaa ccggggtaca tatgattgac    5700
atgctagttt tacgattacc gttcatcgat tctcttgttt gctccagact ctcaggcaat    5760
gacctgatag cctttgtaga gacctctcaa aaatagctac cctctccggc atgaatttat    5820
cagctagaac ggttgaatat catattgatg gtgatttgac tgtctccggc ctttctcacc    5880
cgtttgaatc tttacctaca cattactcag gcattgcatt taaaatatat gagggttcta    5940 aaaatttta tccttgcgtt gaaataaagg cttctcccgc aaaagtatta cagggtcata    6000 atgttttgg tacaaccgat ttagctttat gctctgaggc tttattgctt aattttgcta    6060
attctttgcc ttgcctgtat gatttattgg atgttgcaat tcctgatgcg gtattttctc    6120
cttacgcatc tgtgcggtat ttcacaccgc atatggtgca ctctcagtac aatctgctct    6180
gatgccgcat agttaagcca gccccgacac ccgccaacac ccgctgacgc gccctgacgg    6240
gcttgtctgc tcccggcatc cgcttacaga caagctgtga ccgtctccgg gagctgcatg    6300
tgtcagaggt tttcaccgtc atcaccgaaa cgcgcgagac gaaagggcct cgtgatacgc    6360
ctatttttat aggttaatgt catgataata atggtttctt agacgtcagg tggcactttt    6420
cggggaaatg tgcgcggaac ccctatttgt ttatttttct aaatacattc aaatatgtat    6480
ccgctcatga caataaacc ctgataaatg cttcaataat attgaaaaag gaagagtatg    6540
agtattcaac atttccgtgt cgcccttatt ccctttttg cggcattttg ccttcctgtt    6600
tttgctcacc cagaaacgct ggtgaaagta aaagatgctg aagatcagtt gggtgcacga    6660
gtgggttaca tcgaactgga tctcaacagc ggtaagatcc ttgagagttt tcgccccgaa    6720
gaacgttttc caatgatgag cacttttaaa gttctgctat gtggcgcggt attatcccgt    6780
attgacgccg ggcaagagca actcggtcgc cgcatacact attctcagaa tgacttggtt    6840
gagtactcac cagtcacaga aaagcatctt acggatggca tgacagtaag agaattatgc    6900
agtgctgcca taaccatgag tgataacact gcggccaact tacttctgac aacgatcgga    6960
ggaccgaagg agctaaccgc ttttttgcac aacatggggg atcatgtaac tcgccttgat    7020
cgttgggaac cggagctgaa tgaagccata ccaaacgacg agcgtgacac cacgatgcct    7080
gtagcaatgg caacaacgtt gcgcaaacta ttaactggcg aactacttac tctagcttcc    7140
cggcaacaat taatagactg gatggaggcg gataaagttg caggaccact tctgcgctcg    7200
gcccttccgg ctggctggtt tattgctgat aaatctggag ccggtgagcg tgggtctcgc    7260
ggtatcattg cagcactggg gccagatggt aagccctccc gtatcgtagt tatctacacg    7320
acggggagtc aggcaactat ggatgaacga aatagacaga tcgctgagat aggtgcctca    7380
ctgattaagc attggtaact gtcagaccaa gtttactcat atatacttta gattgattta    7440
aaacttcatt tttaatttaa aaggatctag gtgaagatcc tttttgataa tctcatgacc    7500
aaaatccctt aacgtgagtt ttcgttccac tgagcgtcag accccgtaga aaagatcaaa    7560
ggatcttctt gagatccttt ttttctgcgc gtaatctgct gcttgcaaac aaaaaaacca    7620
ccgctaccag cggtggtttg tttgccggat caagagctac caactctttt tccgaaggta    7680
actggcttca gcagagcgca gataccaaat actgtccttc tagtgtagcc gtagttaggc    7740
caccacttca agaactctgt agcaccgcct acatacctcg ctctgctaat cctgttacca    7800
gtggctgctg ccagtggcga taagtcgtgt cttaccgggt tggactcaag acgatagtta    7860
```

-continued

```
ccggataagg cgcagcggtc gggctgaacg gggggttcgt gcacacagcc cagcttggag    7920
cgaacgacct acaccgaact gagataccta cagcgtgagc tatgagaaag cgccacgctt    7980
cccgaaggga gaaaggcgga caggtatccg gtaagcggca gggtcggaac aggagagcgc    8040
acgagggagc ttccaggggg aaacgcctgg tatctttata gtcctgtcgg gtttcgccac    8100
ctctgacttg agcgtcgatt tttgtgatgc tcgtcagggg ggcggagcct atggaaaaac    8160
gccagcaacg cggccttttt acggttcctg gccttttgct ggccttttgc tcacatgttc    8220
tttcctgcgt tatcccctga ttctgtggat aaccgtatta ccgcctttga gtgagctgat    8280
accgctcgcc gcagccgaac gaccgagcgc agcgagtcag tgagcgagga agcggaagag    8340
cgcccaatac gcaaac                                                   8356

<210> SEQ ID NO 3
<211> LENGTH: 24
<212> TYPE: DNA
<213> ORGANISM: adeno-associated virus 2

<400> SEQUENCE: 3
gatgatgatg atgatgatga cgac                                            24

<210> SEQ ID NO 4
<211> LENGTH: 60
<212> TYPE: DNA
<213> ORGANISM: adeno-associated virus 2

<400> SEQUENCE: 4
gaggaacctg ttaagacgga tgatgatgat gatgatgacg acgctccggg aaaaaagagg    60

<210> SEQ ID NO 5
<211> LENGTH: 20
<212> TYPE: DNA
<213> ORGANISM: adeno-associated virus 2

<400> SEQUENCE: 5
atctcaaccc gtttctgtcg                                                 20

<210> SEQ ID NO 6
<211> LENGTH: 19
<212> TYPE: DNA
<213> ORGANISM: adeno-associated virus 2

<400> SEQUENCE: 6
gcgtctccag tctgaccaa                                                  19

<210> SEQ ID NO 7
<211> LENGTH: 28
<212> TYPE: DNA
<213> ORGANISM: adeno-associated virus 2

<400> SEQUENCE: 7
acagggccat tgatggcctc aacctcct                                        28

<210> SEQ ID NO 8
<211> LENGTH: 30
<212> TYPE: DNA
<213> ORGANISM: adeno-associated virus 2

<400> SEQUENCE: 8
gcttcgtgtg gtcttccaga ttgtgagttg                                      30
```

DELIVERY OF THERAPEUTIC AGENTS TO THE BONE

CROSS REFERENCE TO RELATED APPLICATIONS

This application claims benefit of priority to U.S. Provisional Patent Application No. 61/081,711, filed Jul. 17, 2008, incorporated herein in its entirety by reference.

FIELD OF THE INVENTION

The invention relates to compositions and methods for targeting vectors to bone tissue for the delivery of therapeutic agents, including but not limited to viral vectors, liposomes, and large synthetic and natural polymers, for the delivery of polypeptides, polynucleic acids, and other therapeutic agents.

BACKGROUND OF THE INVENTION

Mucopolysaccharidosis IVA (MPS IVA) is an autosomal recessive disorder caused by deficiency of N-acetylgalactosamine-6-sulfate-sulfatase (GALNS, EC 3.1.6.4), leading to accumulation of glycosaminoglycans (GAGs), keratan sulfate (KS) and chondroitin-6-sulfate (C6S) (For review see; Neufeld et al. (2001) McGraw-Hill: New York. vol III, pp 3421-3452). Clinical manifestations vary from severe to an attenuated form characterized by systemic skeletal dysplasia, laxity of joints, hearing loss, corneal clouding, and heart valvular disease, with normal intelligence. Generally MPS IVA patients do not survive beyond second or third decade of life, although patients with an attenuated form can survive into the seventh decade of life (Montaño et al. (2007) J Inherit Metab Dis., 30: 165-174). Currently, no effective therapies exist for MPS IVA. Surgical interventions are used to treat some manifestations of the disease Id. Although other tissues are affected in MPS IVA patients, an ideal therapeutic agent would be efficiently distributed to bone and bone marrow. Other diseases also exist for which delivery of therapeutic agents to bone would be beneficial. One example is hypophosphotasia, for which the targeted delivery of tissue non-specific alkaline phosphatase (TNSALP) would be highly beneficial. Another example is type VII mucopolysaccharidosis, which would benefit greatly from the targeted delivery of β-glucuronidase (GUS). Gene and enzyme replacement therapy are promising treatments for bone related diseases. However, there exists a need to facilitate the delivery of therapeutic agents including polynucleotides and polypeptides to bone. The inventors provide compositions and methods to promote effective delivery of therapeutic agents to bone using large molecule vectors.

SUMMARY

The present invention relates to methods and compositions for delivering therapeutic agents to bone. More specifically the present invention is directed to endowing large molecule vectors with capable of targeting bone by attaching acid amino acid peptides to these vectors externally.

In the one embodiment, the vector is a viral vector, a liposome, a large synthetic polymer, a large natural polymer, or a polymer comprised of natural and synthetic components, with acid amino acid peptides attached externally. The vector incorporates a therapeutic agent. The therapeutic agent is a pharmaceutical, a nucleotide, or a polypeptide therapeutic agent.

In a preferred embodiment, the vector is adeno-associated virus, with acid amino acid peptides attached externally, and the therapeutic polypeptide is either N-acetylgalactosamine-6-sulfate-sulfatase, tissue non-specific alkaline phosphatase, or β-glucuronidase.

In a most preferred embodiment, the vector is adeno-associated virus, with acid amino acid peptides attached externally, and the therapeutic polypeptide is N-acetylgalactosamine-6-sulfate-sulfatase.

In yet another embodiment, is a method of making an adeno-associated viral vector, targeted to bone, with acid amino acid peptides attached externally, and incorporating a polypeptide therapeutic agent.

DETAILED DESCRIPTION

Figure 1:
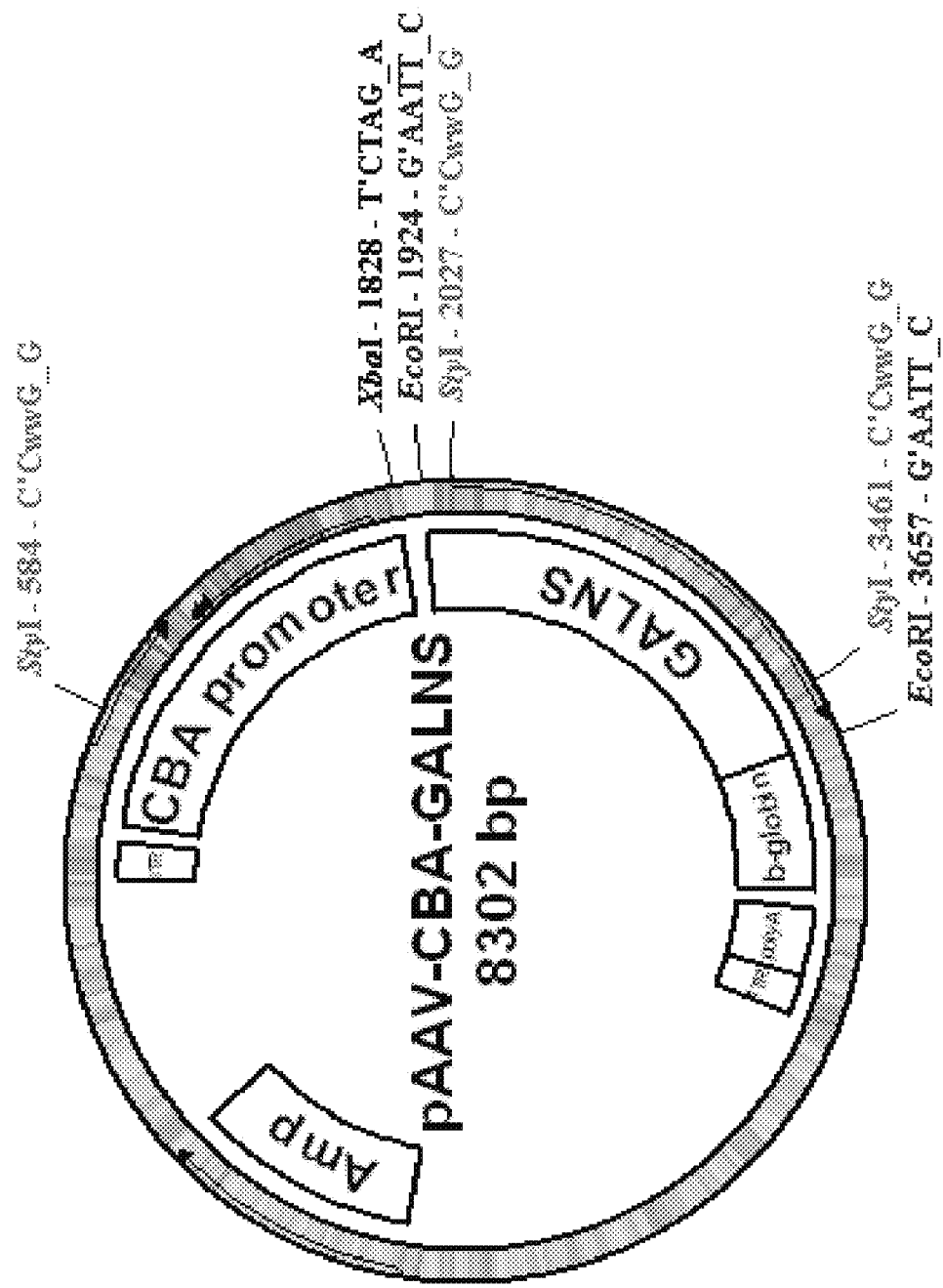
FIG. 1. Map of plasmid pAAV-CBA-GALNS. ITR: inverted terminal repeat, CBA promoter: cytomegalovirus enhancer and β-actin promoter, b-globin: rabbit β-globin polyA, polyA: Fragment containing the bovine growth hormone poly-A signal, Amp: β-lactamase gene.

The inventors have made the surprising discovered that 4-15 acidic amino acid polypeptides, inserted into a large molecule or vector such as adeno-associated virus (AAV) (approximately 5000 KDa), by incorporating the acidic amino acid polypeptides into the AAV capsid, will increase the affinity of this viral vector for bone. Most therapeutic agents intended for bone diseases including AAV, do not have a particular affinity to Bone (Gittensa et al. (2005) *Adv Drug Deliv Rev.* 57: 1011-1036). Bone is distinguished from other tissues by the presence of hydroxyapatite (HA), which is positively charged. The inventors have utilized a peptides of 4-15 acidic amino acid residues (AAA), inserted into a virus capsid to increase the affinity for HA and enhance delivery of the vector nucleotides to bone. As disclosed below, AAA tagged AAV (AAA-AAV), showed 100% binding to HA while the untagged vector showed no binding with HA. In addition, the level of viral gene production after transduction of virus into the cells was not affected by the addition of the AAA peptide. Experiments in mice showed that 48 hours after intravenous infusion of the AAA tagged vector, the virus genome was increased between 16 and 291 fold in bone compared to mice infused with untagged vector.

Adeno-Associated Virus (AAV).

Adeno-associated virus (AAV) are non-enveloped virus with a linear single-stranded DNA of 4.7 kb genome. AAV typically require a helper virus, usually adenovirus or herpesvirus, for replication (Flotte (2004) *Gene Ther* 11: 805-810). The viral capsid protein is the first element that a cellular receptor encounters during a viral infection. Capsid structure for the serotypes AAV2, AAV4, AAV5, and AAV8 has been determined and the regions involved in host receptor interactions have been identified (see Xie et al. (2002) *Proc Natl Acad Sci USA* 99: 10405-10410; Nam et al. (2007) *J Virol* 81: 12260-12271; Choi et al. (2005) *Curr Gen Ther* 5: 299-310). The AAV capsid is formed by 60 proteins consisting of VP1, VP2 and VP3 in a 1:1:20 ratio, respectively, which differ in their N-terminus (Flotte (2004) *Gene Ther* 11: 805-810). Mutagenesis analysis has identified capsid positions which allow the insertion of peptide sequences with little effect on the DNA packaging and virus trafficking. These positions are exposed on the capsid surface (Büning, et al. (2003) *Gene Ther* 10: 1142-1151). For example, in AAV2, the most studied serotype, peptides inserted after amino acid positions 138, 161, 459, 584, 587 and 588, relative to VP1 sequence, are exposed on the viral vector surface. It was seen that modified AAV2 produced viral titers similar to wild-type AAV2 (Büning, et al. (2003) *Gene Ther* 10: 1142-1151)-12; Wu et al. (2000) *J Virol* 74: 8635-8647; Shi et al. (2001) *Hum Gene Ther* 12: 1697-1711). It was reasoned that the attachment of ligands with an affinity for a component of bone such as hydroxyapatite may endow AAV with the ability to target bone and, if attached externally, would not affect the functionality of the virus.

Method of Making Acid Amino Acid-Adeno-Associated Virus (AAA-AAV)

Producing AAA-AAV, involves methodology that is generally known by the skilled artisan and described in detail in numerous laboratory protocols, one of which is Molecular Cloning 3rd edition, (2001) J. F. Sambrook and D. W. Russell, ed., Cold Spring Harbor University Press, incorporated by reference herein in it entirety. Many modifications and variations of the present illustrative DNA sequences and nucleotide vectors are possible. For example, the degeneracy of the genetic code allows for the substitution of nucleotides throughout polypeptide coding regions, as well as in the translational stop signal, without alteration of the encoded polypeptide coding sequence. Such substitutable sequences can be deduced from the known amino acid or DNA sequence. AAA-AAV can be constructed by following conventional synthetic or site-directed mutagenesis procedures. Synthetic methods can be carried out in substantial accordance with the procedures of Itakura et. al., (1977) *Science* 198:1056; and Crea et. al. (1978) *Proc. Natl. Acad. Sci, USA* 75:5765, incorporated by reference herein in their entirety. The present invention is in no way limited to the DNA sequences and plasmids specifically exemplified.

Plasmid Construction.

Figure 2:
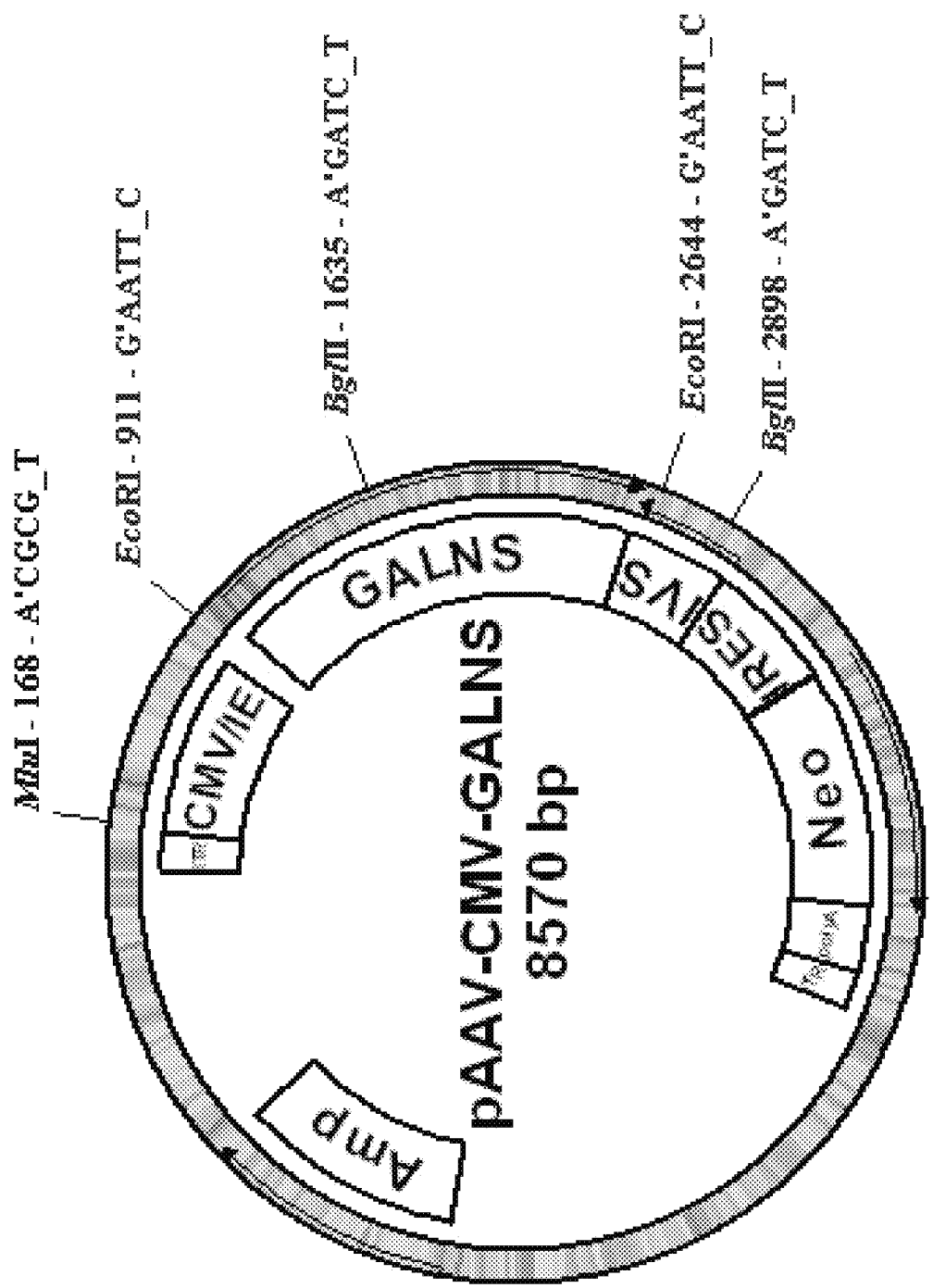
FIG. 2. Map of plasmid pAAV-CMV-GALNS. ITR: inverted terminal repeat, CMV/IE: cytomegalovirus immediate early enhancer/promoter, IVS: Synthetic intron, IRES: Attenuated internal ribosome entry site (IRES) from encephalomyocarditis virus, Neo: Neomycin phosphotransferase coding sequence, polyA: fragment containing the bovine growth hormone poly-A signal, Amp: β-lactamase gene.
Figure 3:
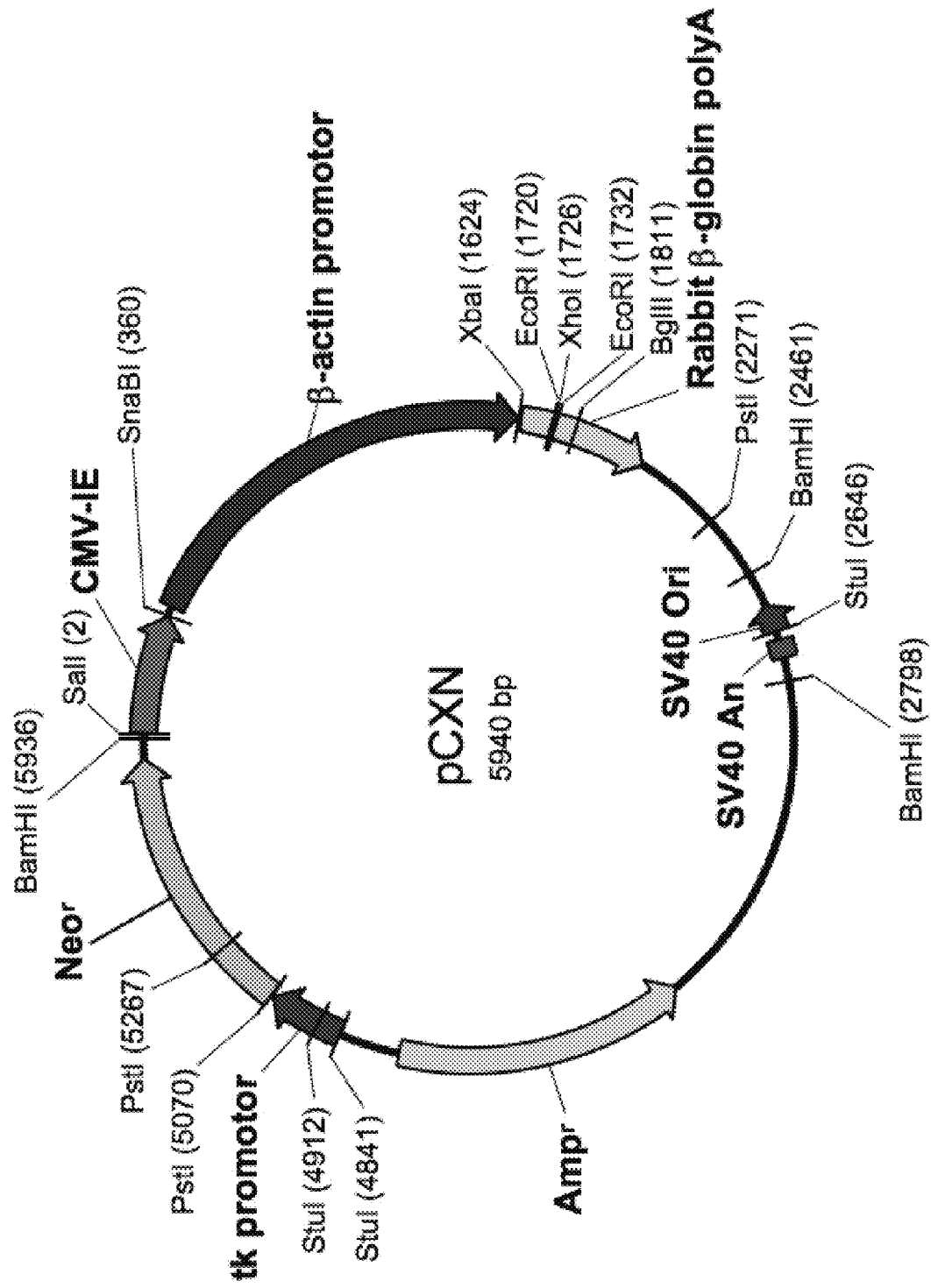
FIG. 3. Map of plasmid pCXN. CMV-IE: cytomegalovirus immediate early enhancer, Amp: β-lactamase, Neo: Neomycin phosphotransferase coding sequence.
Figure 4:
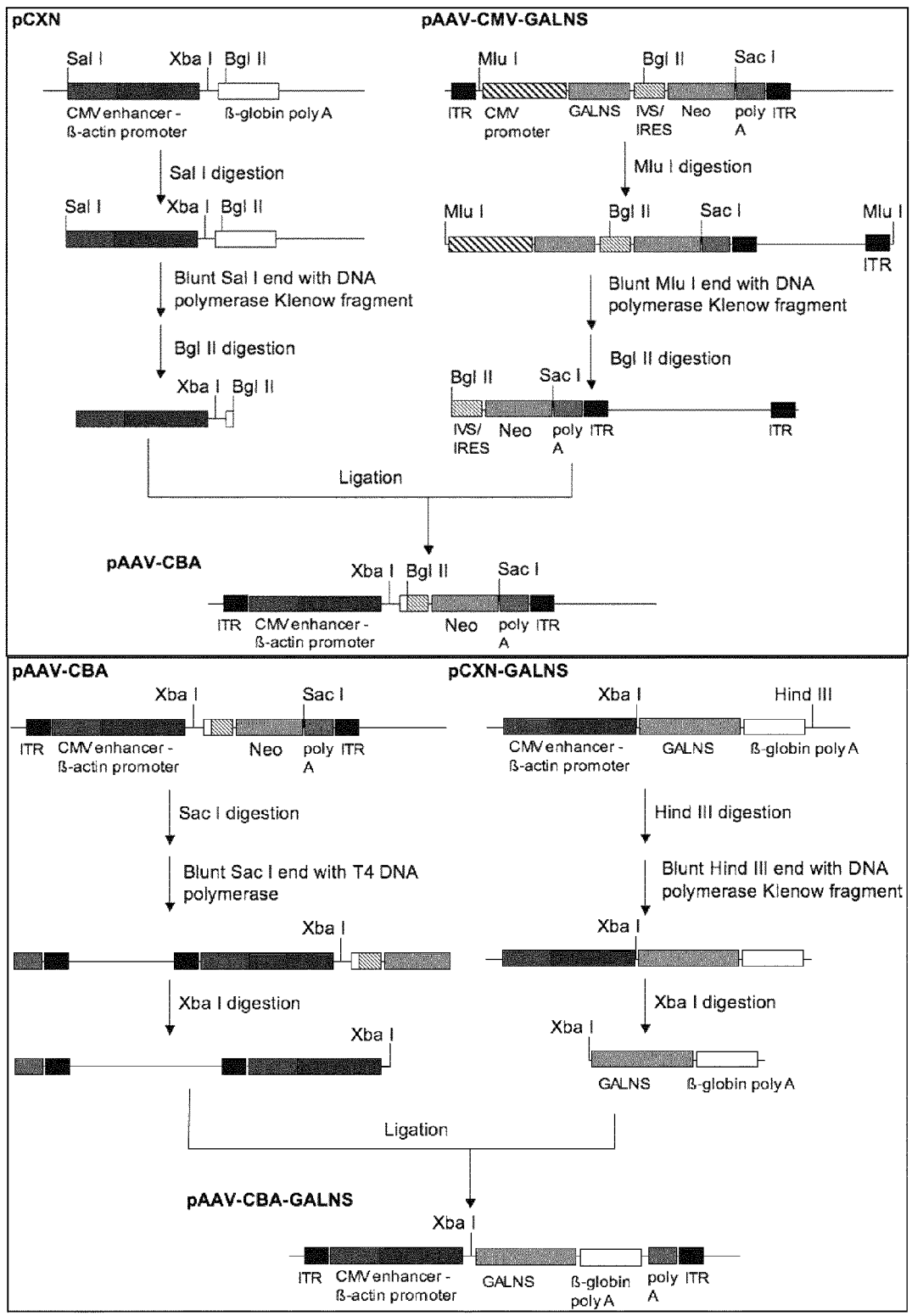
FIG. 4. Scheme of the construction of the plasmid pAAV-CBA-GALNS.

The pAAV-CBA-GALNS plasmid, as illustrated in FIG. 1., incorporates the cytomegalovirus enhancer and β-actin promoter (CBA) to drive expression of the human N-acetylgalactosamine-6-sulphate sulphatase (GALNS). It is flanked by AAV2 ITRs. The plasmid was constructed by replacing the cytomegalovirus immediate early enhancer/promoter (CMV) in pAAV-CMV-GALNS (FIG. 2) as previously constructed with a 1.8-kb fragment from pCXN (FIG. 3) containing the CBA promoter. The CMV immediate early enhancer/promoter in pAAV-CMV-GALNS has been previously described (Niwa et al. (1991) December 15; 108(2):193-9) and is herein incorporated by reference in its entirety. The 1.8-kb fragment was ligated into the plasmid and the correct orientation of the insert was confirmed by restriction enzyme analysis (FIG. 4).

Figure 5:
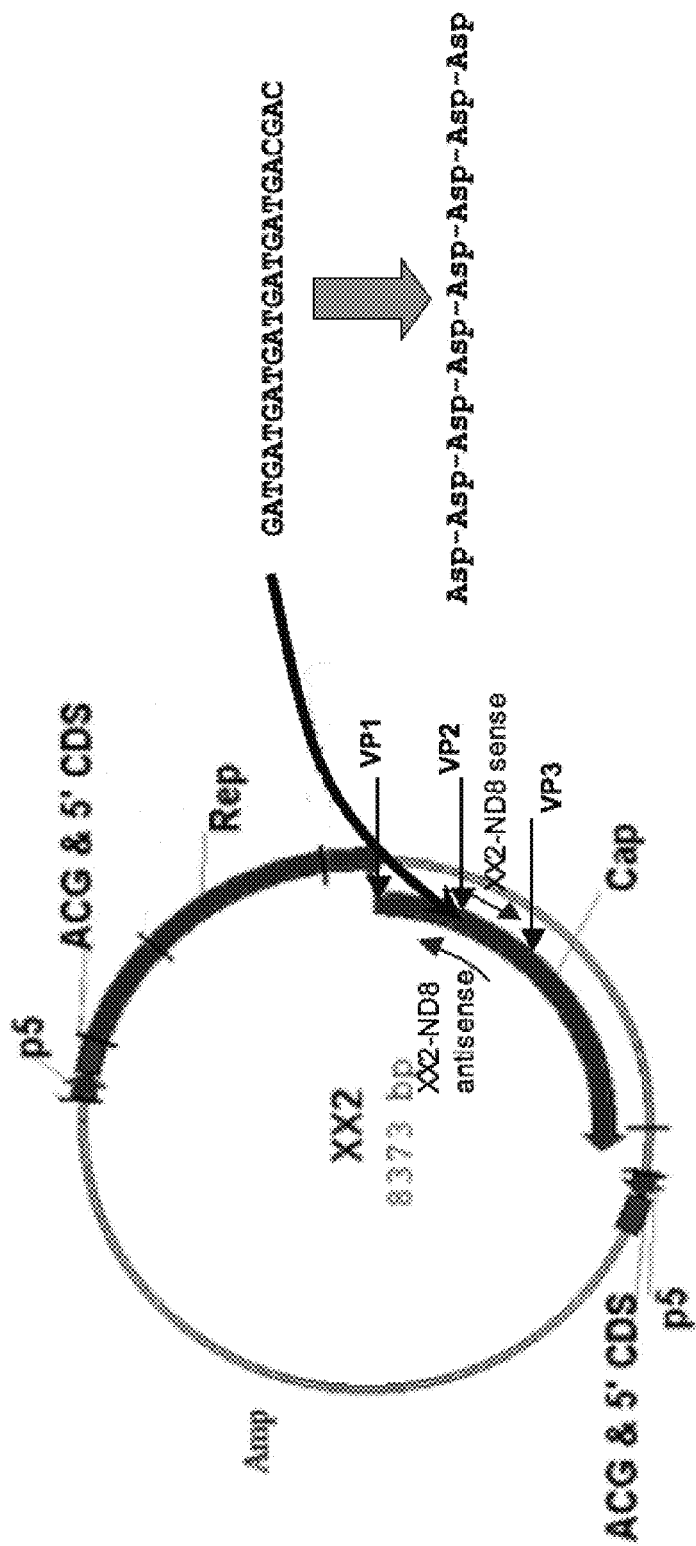
FIG. 5. Insertion of sequence encoding the octapeptide of aspartic amino acids in the pXX2 plasmid. Arrows show the site for the initial codon of VP1, VP2 and VP3.

To produce the AAA-AAV vector which incorporates the octapeptide of aspartic acid in to the capsid protein, the pXX2 plasmid (SEQ ID NO:1) which encodes for the Rep and Cap AAV2 proteins (Xiao et al. (1998) J Virol 72: 2224-2232), was modified to produce (pXX2-ND8) (SEQ ID NO:2). This was done by inserting a sequence encoding eight aspartic amino acids (ND8) (5'-GATGATGATGATGATGATGAC-GAC-3') (SEQ ID NO:3), immediately after the initial codon of the VP2 protein in the packing plasmid pXX (FIG. 5). Insertion was carried out using a commercial site-directed mutagenesis kit (QuikChangee® Site-Directed Mutagenesis Kit, Stratagene, La Jolla, Calif.) according to manufacturer's instructions, by using the primers: 5-gaggaacctgttaagacg-GATGATGATGATGATGATGACGACgctc-cgggaaaaaagagg-3 (SEQ ID NO:4) (XX2-ND8 sense) and its complement (XX2-ND8 antisense). Insertion of the sequence encoding the octapeptide sequence was first confirmed by PCR with primers XX2-ND8-4F 5'-ATCTCAAC-CCGTTTCTGTCG-3' (SEQ ID NO:5) and XX2-ND8-4R 5'-GCGTCTCCAGTCTGACCAA-3'(SEQ ID NO:6), flanking the insertion site, which produced a PCR product of 691 bp with the original pXX2 plasmid and 715 bp after the insertion of sequence. The resulting plasmid (pXX2-ND8) (SEQ ID NO:2) was sequenced to ensure the presence of the eight aspartic amino acids without introduction of fortuitous mutations.

Production of Recombinant AAV-AAV Vectors

CBA-GALNS (native capsid) or ND8/CBA-GALNS (AAA tagged capsid) were produced by calcium phosphate-mediated co-transfection of pAAV-CBA-GALNS, pXX6-80 helper plasmid (Xiao et al. (1998) J Virol 72: 2224-2232), and pXX2 or pXX2-ND8 plasmids (Zolotukhin et al. (1999). *Gene Ther* 6: 973-985). HEK 293 cells were seeded to 80-90% confluence on 15-cm culture plates and media was removed immediately before starting the transfection. The three plasmids were mixed in 18:18:54 µg ratio (1:1:1 molar ratio) with 1.25 mL of 0.25 M $CaCl_2$. Then, 1.25 mL of 2×HeBS buffer (280 mM NaCl, 1.5 mM $Na_2HPO_4$, 50 mM HEPES, pH 7.1) was added and the mixture was incubated for 1 minute at room temperature. The mixture was added to 20 mL of culture media (DMEM with FBS and antibiotics) and immediately dispensed into the culture plate. Forty-eight hours after transfection, the cells were harvested, resuspended in 15 mL of AAV lysis buffer (0.15 M NaCl, 50 mM Tris-HCl pH 8.5), and lysated by three freeze/thaw cycles.

The solution was clarified by centrifugation at 3,700 g at 40 for 20 minutes. The supernatant was designated the primary viral solution and stored at −80° C. for further analysis.

AAV vectors were purified by iodixanol gradient (Zolotukhin et al. (1999) Gene Ther 6: 973-985). The gradient was prepared by combining 9 mL of 15% iodixanol (Optiprep®, Sigma-Aldrich, Saint Louis, Mo.), 1 M NaCl in PBS-MK buffer (1×PBS, 1 mM MgCl$_2$ and 2.5 mM KCl), 6 mL of 25% iodixanol in PBS-MK buffer with Phenol red (2.5 μL of stock solution per mL of iodixanol solution), 5 mL of 40% iodixanol in PBS-MK buffer, and 5 mL of 60% iodixanol in PBS-MK. Primary viral solution (aprox. 15 mL) was added and gradient was centrifuged at 25,000 RPM for 3 h at 18° C. Using a syringe with a 18-gauge needle, 2.5 mL were aspirated of each of the 60% and 40% phases. The virus solution was concentrated with Centricon 100 K (Millipore), desalted with 2 mL of 0.9% NaCl, and stored to −80° C. Quantification was be carried out by a spectrophotometric method, based on the extinction coefficient of the AAV2 capsid proteins and genome (Sommer et al. (2003). Mol Ther 7:122-128). For quantification 100 μL of viral solution was incubated with 0.5 μL of 20% SDS at 75° C. for 10 minutes, and absorbance was measured at 260 and 280 nm. A solution of 0.9% NaCl with 0.5 μL of 20% SDS was used as blank. Virus genomes per mL (vg/mL) were calculated according to the equation:

$$vg/mL = \frac{4.47 \times 10^{19}(A_{260} - 0.59 A_{280})}{MW_{DNA}} \quad (1)$$

where MWDNA is the molecular weight of each viral genome based on its sequence and using the molecular weight of each nucleotide (A=312.2 Da, C=288.2 Da, G=328.2 Da y T=303.2 Da) (see Sommer et al. (2003). Mol Ther 7: 122-128).

In Vitro Transfection.

HEK293 cells, 1×10$^5$ (ATCC CRL-1573) were seeded in 12-well plates and transfected with 1×10$^{10}$ vg (1×10$^5$ vg/cell) of each viral genome. Cells were harvested postransfection, and resuspended in 100 μL of 1% sodium deoxycholate (Sigma-Aldrich, Saint Louis, Mo.). GALNS activity in cell lysate was assayed using the substrate 4-methylumbeliferyl-β-D-galactopyranoside-6-sulphate (Toronto Chemicals Research, North York, On, Canada), as described (van Diggelen et al. (1993) Clin Chem Acta 187:131-140). One unit is defined as the enzyme catalyzing 1 nmol of substrate per hour. Total protein in cell lysate will be determined by micro-Lowry protein assay.

Hydroxyapatite-Binding Assay.

Assays were carried out essentially as described (Nishioka et al. (2006) Mol Genet Metab 88: 244-255). Hydroxyapatite beads (Sigma-Aldrich, Saint Louis, Mo.) were suspended in 25 mM Tris-HCl buffered saline, pH 7.4, at a concentration of 100 μg/μL. AAV2 (wild-type virus), CBA-GALNS and ND8/CBA-GALNS plasmids were mixed at a final concentration 5×10$^{11}$ and 1×10$^{12}$ vg. The mixture was incubated at 37° C. for 1 h, and centrifuged at 14,000 rpm for 10 minutes. The AAV titers were measured in the supernatant, and the bound AAV fraction was determined from the amount of the total and unbound AAV. Quantification of AAV vectors in the supernatant was carried out by the spectrophotometric method described above. Hydroxyapatite-binding assays for each AAV vector was carried out by triplicate.

Biodistribution Experiment.

1.5×10$^{11}$ vg of CBA-GALNS or ND8/CBA-GALNS were injected intravenously into 7-8-weeks-old MPS IVA knockout mice (n=3 for each group) according to Tomatsu et al. (2003) Hum Mol Genet 12: 3349-3358, incorporated by reference herein. Control animals were injected with PBS. Mice were sacrificed 48 hours after the injection, and liver, brain, and bone (leg) were dissected and immediately frozen in dry-ice. Bone marrow was obtained by flushing the femurs with PBS. Genomic DNA was extracted by tissue homogenization in 1 ml of DNAzol (GIBCO, Grand Island, N.Y.) according to manufacturer's instructions. DNA samples from liver, brain, bone and bone marrow were analyzed for the presence of viral DNA by PCR using the primers TOMF23 5'-ACAGGGCCATTGATGGCCTCAACCTCCT-3' (SEQ ID NO:7) and TOMF34R 5'-GCTTCGTGTGGTCTTCCAGATT GTGAGTTG-3'(SEQ ID NO:8), which were specific for human GALNS cDNA, and produced a 235 bp PCR-fragment. This pair-primers specific for human GALNS cDNA, did not amplify the genomic GALNS sequence under these conditions, because the primers annealed in exons 10 and 12, producing a 4.1 kb PCR product. Primers of mouse β-glucuronidase gene were used as an internal control to check DNA quality and absence of PCR-inhibitors. Quantification of the viral genome in bone samples was done by real-time PCR (Tomatsu, et al. (2003) Hum Mol Genet 12: 3349-3358), with a commercial kit, the Fast SYBR® Green Master Mix (Applied Biosystems, Foster City, Calif.), according to manufacturer's instructions, using 1 μg of total DNA and the primers TOMF23 and TOMF34R. The pAAV-CBA-GALNS plasmid was used as standard.

DEFINITIONS

The term "vector" as used herein, refers to vectors for the delivery of therapeutic agents. Examples include, but are not limited to, viral vectors, liposomes, large natural polymers, large synthetic polymers, and polymers comprised of both natural and synthetic components.

The term "therapeutic agent" is intended in its broadest meaning to include not only the polypeptides and polynucleotides of the instance invention but also any agent which conveys an effect beneficial to health including but not limited to any pharmaceutical agent, including cytokines, small molecule drugs, cell-permeable small molecule drugs, hormones, chemotherapy, combinations of interleukins, lectins and other stimulating agents.

The term "polypeptide therapeutic agent" as used herein, refers to any peptide, polypeptide, or protein, with out limitation with therapeutic benefits. By way of example and not of limitation are enzymes which may be useful in enzyme replacement therapy. Non-limiting examples include N-acetylgalactosamine-6-sulfate-sulfatase (GALNS), also described in U.S. patent application Ser. No. 10/864,758, and tissue non-specific alkaline phosphatase (TNSALP) also described in U.S. patent application Ser. No. 11/484,870, and β-glucuronidase (GUS), also described in Ser. No. 11/614, 970. Polypeptide therapeutic agents may include enzymes in their native form, or functional fragments thereof. Polypeptide therapeutic agents may be used alone, or in combination or incorporated into fusion proteins.

The term "acidic amino acid" or "AAA" as used herein, refers to any repeating amino acid sequence of glutamic acid or aspartic acid. As used herein AAA may comprise multiple copies of acidic amino acid peptides, in any arbitrary combination including repeating glutamic acid or aspartic acid sequences or a combination thereof. The number of acid amino acids in each AAA peptide may be 4, 5, 6, 7, 8, 9, 10, 11, 12, 13, 14, or 15. Preferably 4-15, more preferably 4-8, and most preferably 8 acid amino acids. Multiple copies of a peptide consisting of AAA may be directly attached to a vector (viral and non-viral) via a peptide bond or the like. In the present invention, though there is no specific limitation as to the method for attaching multiple copies of a AAA peptide to a vector, it is advantageous, e.g., to produce and use fusion proteins of comprising the vector and the AAA peptide.

The term "large polymer" as used herein, refers to any polymer which may be used to deliver a therapeutic agent. Non-limiting examples of polymers and methods of modification may be found in International Patent Applications Nos. WO/2007/012013 and WO/2004/022099 incorporated by reference herein.

In addition to HEK 293 cells described herein, any number of cell lines are know in the art are capable of expressing the various polynucleotides and plasmids in the invention. To this end, any eukaryotic host cells which possess the cellular machinery for proper processing of the primary transcript may be used. Cell culture techniques are also well known in the art.

Other Large Molecule Vectors.

The instant invention is not limited to AAV. The surprising discovery that AAA peptides may endow large molecules with an affinity for hydroxyapatite (HA) may be applied to other virus or large molecule vectors including any virus vector, by way of example but not of limitation, adenoviruses, retro viruses, HCV, HIV, herpesvirus, papovavirus, poxvirus hepadnavirus, adeno-associated virus, parvovirus, vaccinia virus, etc. or related or derived viruses thereof. Mutant herpesviruses can for example be based on HSV1, HSV2, VZV, CMV, EBV, HHV6, HHV7, or on non-human animal herpesviruses such as PRY, IBRV/BHV, MDV, EHV, and others. Vectors may also include Lentiviruses which have been used for delivery of small interfering RNA as described (Li and Rossi (2005) *Methods Enzymol* 392, 226), hereby incorporated by reference in its entirety. AAA peptides may be inserted into, capsid or coat proteins of any of the aforementioned viral vectors, as described herein for AAV, whereby the virus vector is endowed with an increased affinity for HA.

Also included are any and all vectors derived from liposomes, micelles, or large natural or synthetic polymers. Methods of attaching polypeptides to liposomes are know in the art and may be adapted to the AAA peptides of the instant invention. By way of example but not of limitation, AAA peptides may be fused with transmembrane proteins using methods described in U.S. Pat. No. 5,374,548, incorporated herein by reference in its entirety. Other methods include chemical linking AAA to liposomes, using methods described in U.S. Pat. No. 5,401,511, incorporated herein by reference in its entirety. Other gene delivery vectors include liposome-derived systems, artificial viral envelopes, and other systems known in the art (See, e.g., Rossi, J. J. (1995) Br. Med. Bull. 51(1):217-225; Boado, R. J. et al. (1998) J. Pharm. Sci. 87(11):1308-1315; and Morris, M. C. et al. (1997) Nucleic Acids Res. 25(14):2730-2736; El-Aneed, (2004) J Control Release 94, 1-14), all, herein incorporated by reference in its entirety.

These same chemical linking methods may be applied to large natural and synthetic polymers. By way of example, but not of limitation, natural polymers include polymers derived proteins including collagen and fibrin, or, carbohydrates including hyaluronic acid and sulfated glycosaminoglycans, as well as polymers derived from lipids including liposome or micelles, or polymers derived from polyamino acids including poly-L-arginine, poly-L-lysine and poly-L-ornithine. By way of example but not of limitation, synthetic polymers may include poly(methyl methacrylate) (PMMA), and poly(hydroxyethyl methacrylic) poly(HEMA), or derivatives thereof.

By way of example but not of limitation, polymers which are combinations of synthetic and natural polymers include HEMA-PC and pMPC as described in International Patent Application publication WO 2007/100902, and hereby incorporated by reference in its entirety.

The skilled artisan will recognize that amino acid coupling to proteins or synthetic polymers differ, and conditions will be varied as necessary to promote the formation of the conjugates. Additional guidance maybe obtained from texts such as Wong, 8.S., "Chemistry of Protein Conjugation and Cross-Linking," (CRC Press 1991), or standard texts in organic chemistry.

In one embodiment is a vector with 4-15 acid amino acids attached externally, incorporating a therapeutic agent.

In another embodiment is a viral vector with 4-15 acid amino acids attached externally, incorporating a nucleic acid encoding a polypeptide therapeutic agent. Examples of polypeptide therapeutic agent include, N-acetylgalactosamine-6-sulfate-sulfatase (GALNS), tissue non-specific alkaline phosphatase (TNSALP), and β-glucuronidase (GUS) alone or in combination.

In one preferred embodiment is an adeno-associated virus with 4-15 acid amino acids attached externally, incorporating a nucleic acid encoding N-acetylgalactosamine-6-sulfate-sulfatase (GALNS).

In another embodiment is an adeno-associated virus with 4-15 acid amino acids attached externally, incorporating a nucleic acid encoding tissue non-specific alkaline phosphatase (TNSALP).

In another embodiment is an adeno-associated virus with 4-15 acid amino acids attached externally, incorporating a nucleic acid encoding p-glucuronidase (GUS).

In one embodiment is a method of making a viral vector which targets bone by incorporating 4-15 acid amino acids into the viral capsid.

In another embodiment is a method of treating a subject in need by administering a viral vector with 4-15 acid amino acids attached externally and incorporating a therapeutic agent.

In another embodiment is a liposome with 4-15 acid amino acids attached externally, incorporating a therapeutic agent.

In another embodiment is a synthetic polymer with 4-15 acid amino acids attached externally, incorporating a therapeutic agent.

In another embodiment is a natural polymer with 4-15 acid amino acids attached externally, incorporating a therapeutic agent.

In another embodiment is a polymer with both natural and synthetic components with 4-15 acid amino acids attached externally, incorporating a therapeutic agent.

Methods of Practicing the Invention

Administration

An AAA-AAV vector of the present invention may be prepared in the form of a pharmaceutical composition containing the fusion protein dissolved or dispersed in a pharmaceutically acceptable carrier well known to those who are skilled in the art, for parenteral administration by e.g., intravenous, subcutaneous, or intramuscular injection or by intravenous drip infusion. For the pharmaceutical composition for parenteral administration, any conventional additives may be used such as excipients, binders, disintegrates, dispersing agents, lubricants, diluents, absorption enhancers, buffering agents, surfactants, solubilizing agents, preservatives, emulsifiers, isotonizers, stabilizers, solubilizers for injection, pH adjusting agents, etc. An AAA viral, liposomal, or polymer vector of the present invention, in particular a AAA-AAV viral vector and a AAA peptide attached to a viral capsid, may be used advantageously in place of the conventional untagged (native) viral vector in a substitution therapy for the treatment of bone diseases. In the treatment, the vector carrying the fusion protein may be administered intravenously, subcutaneously, or intramuscularly. Doses and frequencies of administration are to be determined by the physician in charge in accordance with the condition of his or her patient.

The various embodiment described herein are water-soluble and maybe administered, by way of example, in a sterile aqueous solution, preferably a physiological solution. A pharmaceutically acceptable formulation of the present invention may be any injectable or topically applied physiological solution. A physiological solution may be comprised of isotonic balanced salts with a pH of about 7.0 to about 7.5. A preferred physiological solution may comprise isotonic saline and a pH of 7.5. For topical administration or for certain targeted applications it may be desirable to increase the viscosity of the formulation. Various carriers known to increase viscosity include but are not limited to such high molecular weight polymers such as, hyaluronic acid, hydroxypropyl methyl cellulose, as well as other carbohydrates or sugars. These are typical included in the formulation at 0.01 to 0.1 percent, 0.1 to 1.0 percent, 1 to 2 percent, 2 to 3 percent, 3 to 4 percent, 4 to 5 percent 5 to 10 percent, or 10 to 20 percent by weight. By way of example and not of limitation, recombinant viruses may be administered at a dose of $10^7$-$10^{12}$ pfu for a non-intravenous administration.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLES

Example 1

Construction of pXX2-ND8 Plasmid

Figure 6:
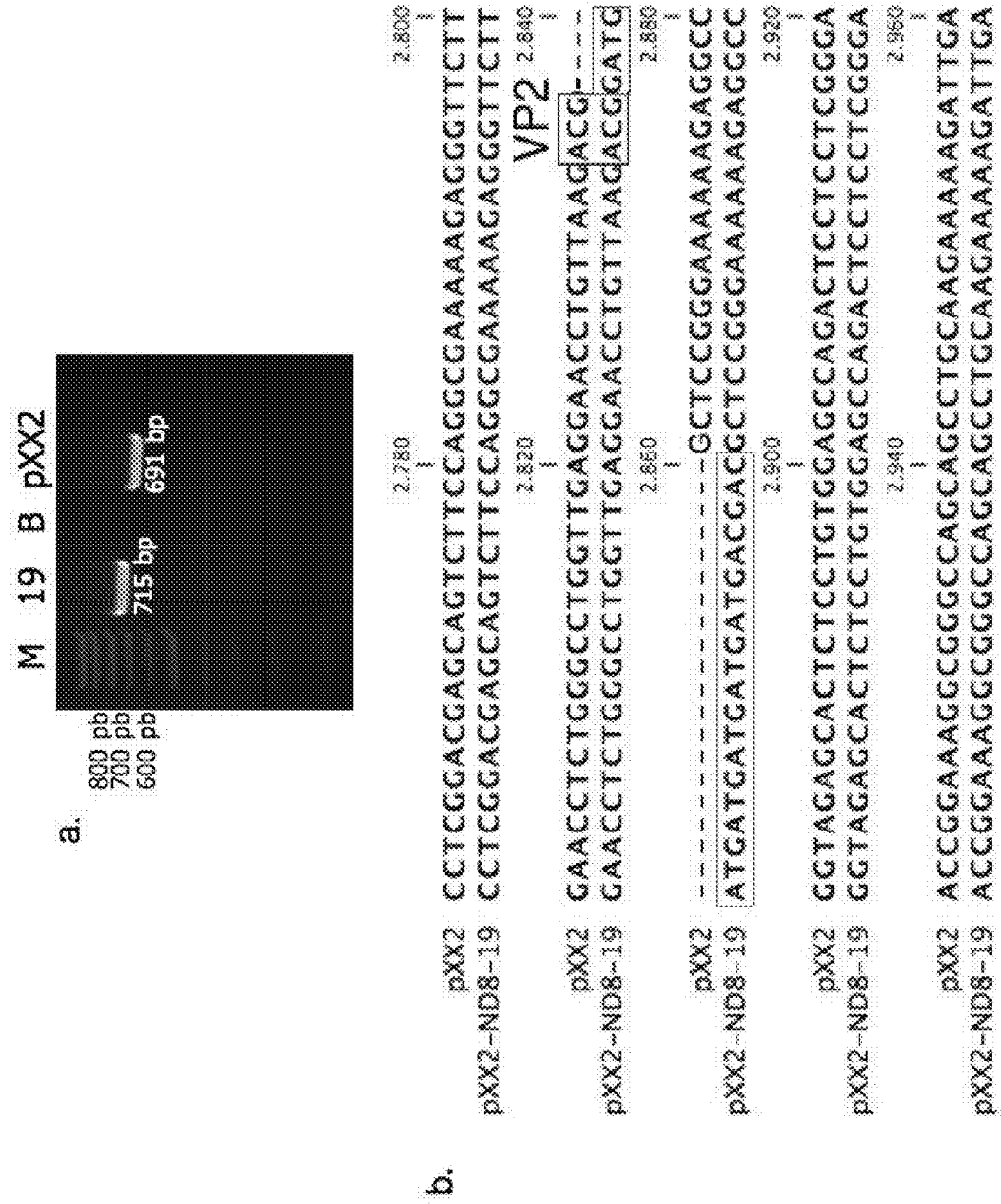
FIG. 6. Construction of pXX2-ND8 plasmid. (a) Positive clone after site-directed mutagenesis was screened by PCR using primers flanking the insertion site. The 715-bp fragment was produced for the targeted clone compared to the 691-bp fragment from pXX2 plasmid. Marker: 100 bp ladder. (b) Alignment of sequencing result of pXX2 and clone 19. A box (single strand) designates the insertion site and the nucleotide sequence encoding eight aspartic amino acids in clone 19.

After site-directed mutagenesis was performed, 20 clones were obtained. Five clones out of 20 clones had an expected size of 8.3 kb. PCR with XX2-ND8-4F and XX2-ND8-4R primers showed that in three clones a PCR product of 715 bp was obtained (FIG. 6a). Sequencing of those plasmids showed the presence of the precise insertional sequence in one clone (FIG. 6b) without introduction of fortuitous mutations.

Example 2

In Vitro Transfection

Figure 7:
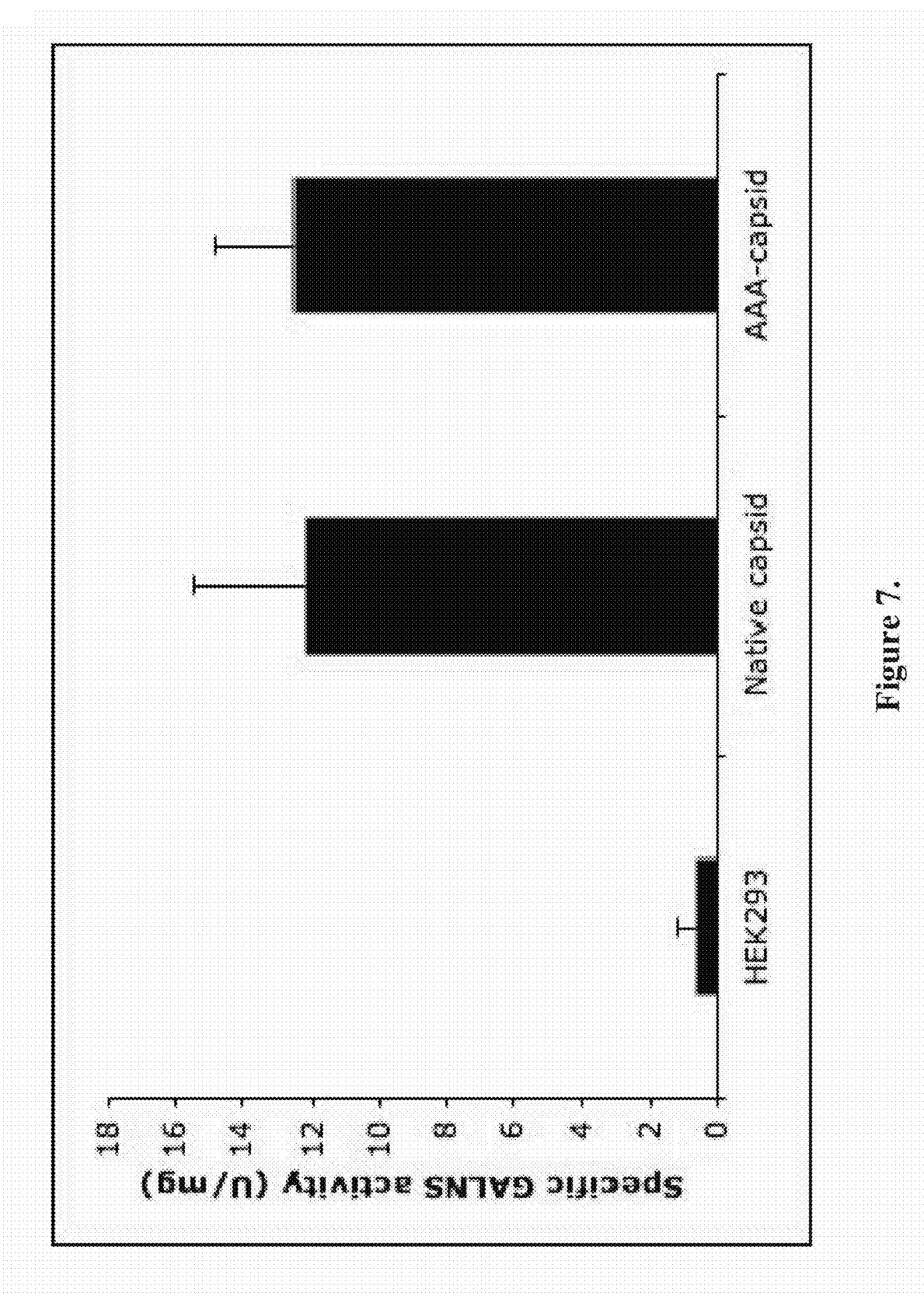
FIG. 7. Transfection of HEK293 cells. HEK293 cells were transfected with $1 \times 10^{10}$ vg of the unmodified native AAV capsid or the modified AAV-AAA-capsid. GALNS activity in the cell lysate was assayed after 4 days of post-transfection.

GALNS activity from transfected cells with either untagged or tagged plasmid increased to 12.24+/−3.25 U/mg or 12.53+/−2.33 U/mg respectively, compared to 0.63+/−0.55 U/mg in untransfected cells (FIG. 7). These results show that the presence of the AAA in the capsid does not alter the transfection efficacy of the plasmid and expression level of the gene product.

Example 3

Hydroxyapatite-Binding Assay

Figure 8:
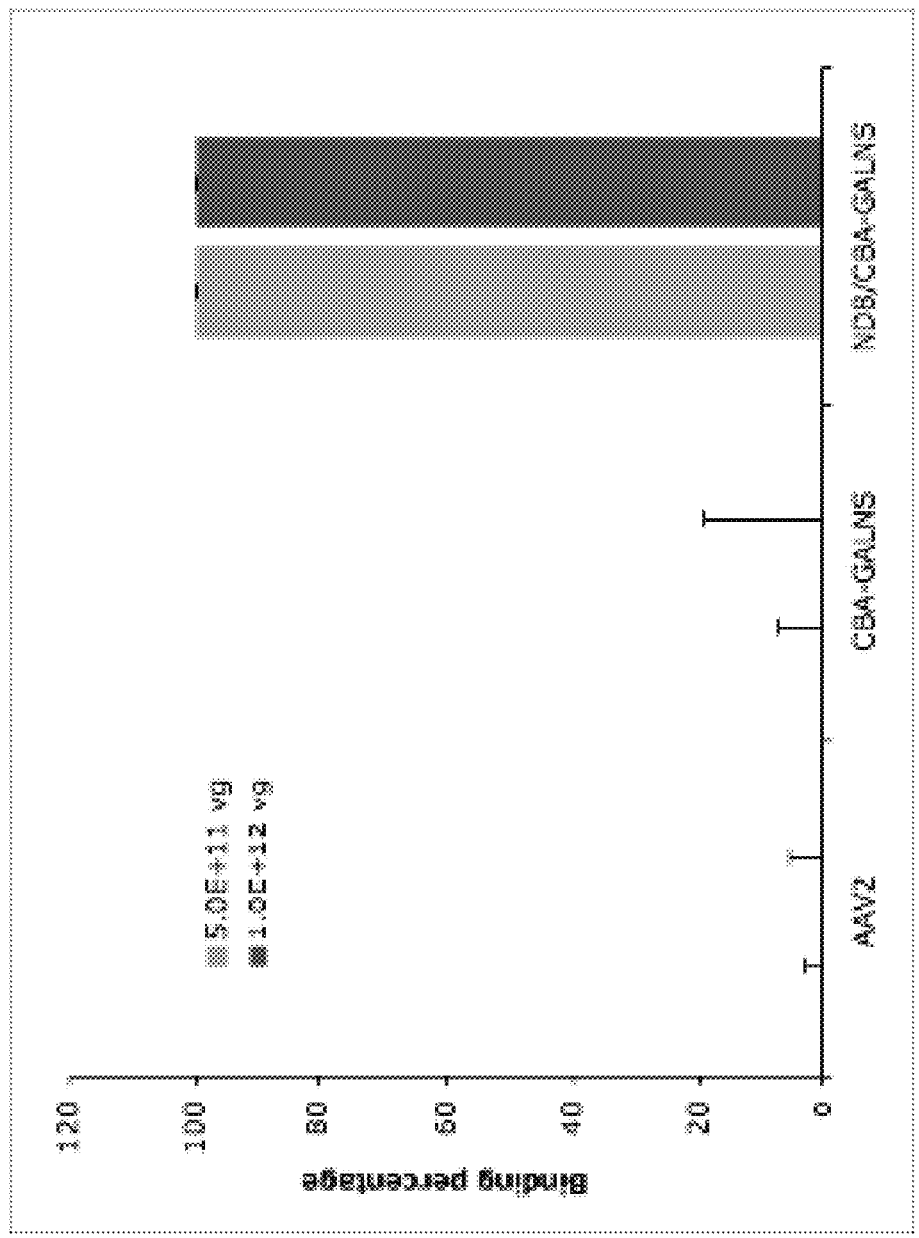
FIG. 8. Hydroxyapatite-binding assay. Hydroxyapatite beads were incubated with $5 \times 10^{11}$ vg (blue, n=3) or $1 \times 10^{12}$ vg (red, n=3) of each virus for 1 h at 37° C. After centrifugation virus titers were quantified in the supernatant by spectrophotometric method, and compared with the initial amount of virus mixed.

AAV2 wild-type and CBA-GALNS (native capsid) virus vectors were found in all 100% in the supernatant after the hydroxyapatite-binding assay indicating no binding with hydroxyapatite, while no ND8/CBA-GALNS virus vectors were was found in the supernatant, indicating 100% affinity with hydroxyapatite (FIG. 8).

Example 4

Biodistribution Experiment

Figure 9:
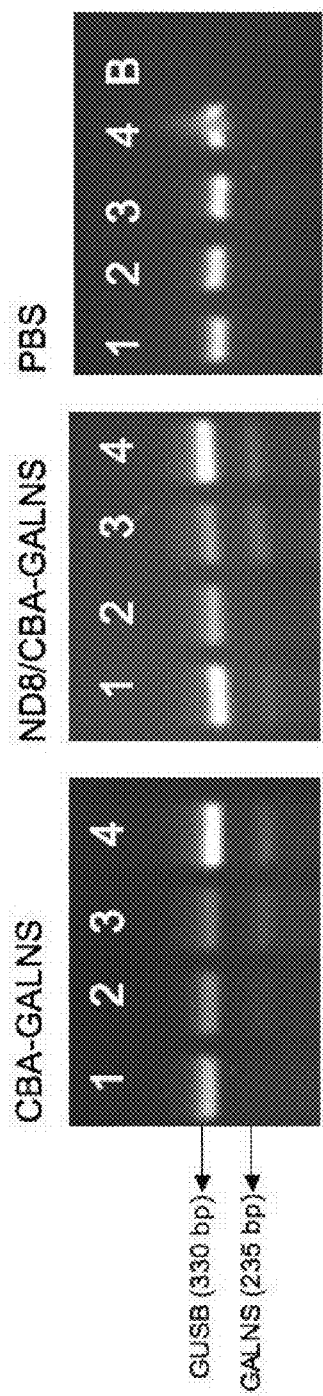
FIG. 9. Biodistribution experiment. Mice were sacrificed 48 h after a vein tail infusion of $1.5 \times 10^{11}$ vg. 1 μg of DNA samples from bone (1), liver (2), brain (3) and bone marrow (4) were subjected to PCR using specific primers for GALNS cDNA. Primers for mouse β-glucuronidase (GUS) were used as internal control to check DNA quality and absence of PCR-inhibitors

DNA samples from bone, liver, brain and bone marrow were tested by PCR for presence of vector DNA after 48 h. After 48 h post injection, virus DNA was detected in liver, brain, and bone marrow with both CBA-GALNS and ND8/CBA-GALNS vectors. However, in bone with ND8/CBA-GALNS, the virus genome was detected while CBA-GALNS, was not detected (FIG. 9). Although mouse-by-mouse variation was observed, virus genome quantification by real-time PCR in DNA samples from bone showed an increment between 16- and 291-folds in the amount of virus genome in mice infused with ND8/CBA-GALNS compared to mice infused with CBA-GALNS. No virus DNA was detected in any tissue sample from control mice with PBS.

All publications and patents cited in this specification including U.S. patent application Ser. Nos., 11/614,970, 11/245,424, 11/484,870, 60/725,563, and 10/864,758, are hereby incorporated by reference in their entirety. The discussion of the references herein is intended merely to summarize the assertions made by the authors and no admission is made that any reference constitutes prior art. Applicants reserve the right to challenge the accuracy and pertinence of the cited references.

Sequences

SEQ ID NO: 1. Complete sequence of packing plasmid pXX2 (8.3 kb). Initial codon for capsid proteins VP1, VP2 and VP3 are shown in bold.

```
CGCCTCTCCCCGCGCGTTGGCCGATTCATTAATGCAGAATTCCCATCATC

AATAATATACCTTATTTTGGATTGAAGCCAATATGATAATGAGGGGGTGG

AGTTTGTGACGTGGCGCGGGCGTGGGAACGGGGCGGGTGACGTAGTAGC

TCTAGAGGTCCTGTATTAGAGGTCACGTGAGTGTTTTGCGACATTTTGCG

ACACCATGTGGTCACGCTGGGTATTTAAGCCCGAGTGAGCACGCAGGGTC

TCCATTTTGAAGCGGGAGGTTTGAACGCGCAGCCACCACGGCGGGGTTTT

ACGAGATTGTGATTAAGGTCCCCAGCGACCTTGACGAGCATCTGCCCGGC

ATTTCTGACAGCTTTGTGAACTGGGTGGCCGAGAAGGAATGGGAGTTGCC

GCCAGATTCTGACATGGATCTGAATCTGATTGAGCAGGCACCCCTGACCG

TGGCCGAGAAGCTGCAGCGCGACTTTCTGACGGAATGGCGCCGTGTGAGT

AAGGCCCCGGAGGCCCTTTTCTTTGTGCAATTTGAGAAGGGAGAGAGCTA

CTTCCACATGCACGTGCTCGTGGAAACCACCGGGGTGAAATCCATGGTTT

TGGGACGTTTCCTGAGTCAGATTCGCGAAAAACTGATTCAGAGAATTTAC

CGCGGGATCGAGCCGACTTTGCCAAACTGGTTCGCGGTCACAAAGACCAG

AAATGGCGCCGGAGGCGGGAACAAGGTGGTGGATGAGTGCTACATCCCCA

ATTACTTGCTCCCCAAAACCCAGCCTGAGCTCCAGTGGGCGTGGACTAAT

ATGGAACAGTATTTAAGCGCCTGTTTGAATCTCACGGAGCGTAAACGGTT

GGTGGCGCAGCATCTGACGCACGTGTCGCAGACGCAGGAGCAGAACAAAG
```

-continued

```
AGAATCAGAATCCCAATTCTGATGCGCCGGTGATCAGATCAAAAACTTCA
GCCAGGTACATGGAGCTGGTCGGGTGGCTCGTGGACAAGGGGATTACCTC
GGAGAAGCAGTGGATCCAGGAGGACCAGGCCTCATACATCTCCTTCAATG
CGGCCTCCAACTCGCGGTCCCAAATCAAGGCTGCCTTGGACAATGGGGGA
AAGATTATGAGCCTGACTAAAACCGCCCCCGACTACCTGGTGGGCCAGCA
GCCCGTGGAGGACATTTCCAGCAATCGGATTTATAAAATTTTGGAACTAA
ACGGGTACGATCCCCAATATGCGGCTTCCGTCTTTCTGGGATGGGCCACG
AAAAAGTTCGGCAAGAGGAACACCATCTGGCTGTTTGGGCCTGCAACTAC
CGGGAAGACCAACATCGCGGAGGCCATAGCCCACACTGTGCCCTTCTACG
GGTGCGTAAACTGGACCAATGAGAACTTTCCCTTCAACGACTGTGTCGAC
AAGATGGTGATCTGGTGGGAGGAGGGGAAGATGACCGCCAAGGTCGTGGA
GTCGGCCAAAGCCATTCTCGGAGGAAGCAAGGTGCGCGTGGACCAGAAAT
GCAAGTCCTCGGCCCAGATAGACCCGACTCCCGTGATCGTCACCTCCAAC
ACCAACATGTGCGCCGTGATTGACGGGAACTCAACGACCTTCGAACACCA
GCAGCCGTTGCAAGACCGGATGTTCAAATTTGAACTCACCCGCCGTCTGG
ATCATGACTTTGGGAAGGTCACCAAGCAGGAAGTCAAAGACTTTTTCCGG
TGGGCAAAGGATCACGTGGTTGAGGTGGAGCATGAATTCTACGTCAAAAA
GGGTGGAGCCAAGAAAAGACCCGCCCCCAGTGACGCAGATATAAGTGAGC
CCAAACGGGTGCGCGAGTCAGTTGCGCAGCCATCGACGTCAGACGCGGAA
GCTTCGATCAACTACGCAGACAGGTACCAAAACAAATGTTCTCGTCACGT
GGGCATGAATCTGATGCTGTTTCCCTGCAGACAATGCGAGAGAATGAATC
AGAATTCAAATATCTGCTTCACTCACGGACAGAAAGACTGTTTAGAGTGC
TTTCCCGTGTCAGAATCTCAACCCGTTTCTGTCGTCAAAAAGGCGTATCA
GAAACTGTGCTACATTCATCATATCATGGGAAAGGTGCCAGACGCTTGCA
CTGCCTGCGATCTGGTCAATGTGGATTTGGATGACTGCATCTTTGAACAA
TAAATGATTTAAATCAGGTATGGCTGCCGATGGTTATCTTCCAGATTGGC
TCGAGGACACTCTCTCTGAAGGAATAAGACAGTGGTGGAAGCTCAAACCT
GGCCCACCACCACCAAAGCCCGCAGAGCGGCATAAGGACGACAGCAGGGG
TCTTGTGCTTCCTGGGTACAAGTACCTCGGACCCTTCAACGGACTCGACA
AGGGAGAGCCGGTCAACGAGGCAGACGCCGCGGCCCTCGAGCACGACAAA
GCCTACGACCGGCAGCTCGACAGCGGGAGACAACCCGTACCTCAAGTACAA
CCACGCCGACGCGGAGTTTCAGGAGCGCCTTAAAGAAGATACGTCTTTTG
GGGGCAACCTCGGACGAGCAGTCTTCCAGGCGAAAAAGAGGGTTCTTGAA
CCTCTGGGCCTGGTTGAGGAACCTGTTAAGACGGCTCCGGGAAAAAGAG
GCCGGTAGAGCACTCTCCTGTGGAGCCAGACTCCTCCTCGGGAACCGGAA
AGGCGGGCCAGCAGCCTGCAAGAAAAAGATTGAATTTTGGTCAGACTGGA
GACGCAGACTCAGTACCTGACCCCCAGCCTCTCGGACAGCCACCAGCAGC
CCCCTCTGGTCTGGGAACTAATACGATGGCTACAGGCAGTGGCGCACCAA
TGGCAGACAATAACGAGGGCGCCGACGGAGTGGGTAATTCCTCGGGAAAT
TGGCATTGCGATTCCACATGGATGGGCGACAGAGTCATCACCACCAGCAC
CCGAACCTGGGCCCTGCCCACCTACAACAACCACCTCTACAAACAAATTT
```

```
CCAGCCAATCAGGAGCCTCGAACGACAATCACTACTTTGGCTACAGCACC
CCTTGGGGGTATTTTGACTTCAACAGATTCCACTGCCACTTTTCACCACG
TGACTGGCAAAGACTCATCAACAACAACTGGGGATTCCGACCCAAGAGAC
TCAACTTCAAGCTCTTTAACATTCAAGTCAAAGAGGTCACGCAGAATGAC
GGTACGACGACGATTGCCAATAACCTTACCAGCACGGTTCAGGTGTTTAC
TGACTCGGAGTACCAGCTCCCGTACGTCCTCGGCTCGGCGCATCAAGGAT
GCCTCCCGCCGTTCCCAGCAGACGTCTTCATGGTGCCACAGTATGGATAC
CTCACCCTGAACAACGGGAGTCAGGCAGTAGGACGCTCTTCATTTTACTG
CCTGGAGTACTTTCCTTCTCAGATGCTGCGTACCGGAAACAACTTTACCT
TCAGCTACACTTTTGAGGACGTTCCTTTCCACAGCAGCTACGCTCACAGC
CAGAGTCTGGACCGTCTCATGAATCCTCTCATCGACCAGTACCTGTATTA
CTTGAGCAGAACAAACACTCCAAGTGGAACCACCACGCAGTCAAGGCTTC
AGTTTTCTCAGGCCGGAGCGAGTGACATTCGGGACCAGTCTAGGAACTGG
CTTCCTGGACCCTGTTACCGCCAGCAGCGAGTATCAAAGACATCTGCGGA
TAACAACAACAGTGAATACTCGTGGACTGGAGCTACCAAGTACCACCTCA
ATGGCAGAGACTCTCTGGTGAATCCGGGCGCGGCCATGGCAAGCCACAAG
GACGATGAAGAAAAGTTTTTTCCTCAGAGCGGGGTTCTCATCTTTGGGAA
GCAAGGCTCAGAGAAAACAAATGTGGACATTGAAAAGGTCATGATTACAG
ACGAAGAGGAAATCAGGACAACCAATCCCGTGGCTACGGAGCAGTATGGT
TCTGTATCTACCAACCTCCAGAGAGGCAACAGACAAGCAGCTACCGCAGA
TGTCAACACACAAGGCGTTCTTCCAGGCATGGTCTGGCAGGACAGAGATG
TGTACCTTCAGGGGCCCATCTGGGCAAAGATTCCACACACGGACGGACAT
TTTCACCCCTCTCCCCTCATGGGTGGATTCGGACTTAAACACCCTCCTCC
ACAGATTCTCATCAAGAACACCCCGGTACCTGCGAATCCTTCGACCACCT
TCAGTGCGGCAAAGTTTGCTTCCTTCATCACACAGTACTCCACGGGACAG
GTCAGCGTGGAGATCGAGTGGGAGCTGCAGAAGGAAAACAGCAAACGCTG
GAATCCCGAAATTCAGTACACTTCCAACTACAACAAGTCTGTTAATGTGG
ACTTTACTGTGGACACTAATGGCGTGTATTCAGAGCCTCGCCCCATTGGC
ACCAGATACCTGACTCGTAATCTGTAATTGCTTGTTAATCAATAAACCGT
TTAATTCGTTTCAGTTGAACTTTGGTCTCTGCGTATTTCTTTCTTATCTA
GTTTCCATGCTCTAGAGGTCCTGTATTAGAGGTCACGTGAGTGTTTTGCG
ACATTTTGCGACACCATGTGGTCACGCTGGGTATTTAAGCCCGAGTGAGC
ACGCAGGGTCTCCATTTTGAAGCGGGAGGTTTGAACGCGCAGCCACCACG
GCGGGGTTTTACGAGATTGTGATTAAGGTCCCCAGCGACCTTGACGAGCA
TCTGCCCGGCATTTCTGACAGCTTTGTGAACTGGGTGGCCGAGAAGGAAT
GGGAGTTGCCGCCAGATTCTGACATGGATCTGAATCTGATTGAGCAGGCA
CCCCTGACCGTGGCCGAGAAGCTGCATCGCTGGCGTAATAGCGAAGAGGC
CCGCACCGATCGCCCTTCCCAACAGTTGCGCAGCCTGAATGGCGAATGGC
GATTCCGTTGCAATGGCTGGCGGTAATATTGTTCTGGATATTACCAGCAA
GGCCGATAGTTTGAGTTCTTCTACTCAGGCAAGTGATGTTATTACTAATC
```

```
AAAGAAGTATTGCGACAACGGTTAATTTGCGTGATGGACAGACTCTTTTA
CTCGGTGGCCTCACTGATTATAAAAACACTTCTCAGGATTCTGGCGTACC
GTTCCTGTCTAAAATCCCTTTAATCGGCCTCCTGTTTAGCTCCCGCTCTG
ATTCTAACGAGGAAAGCACGTTATACGTGCTCGTCAAAGCAACCATAGTA
CGCGCCCTGTAGCGGCGCATTAAGCGCGGCGGGTGTGGTGGTTACGCGCA
GCGTGACCGCTACACTTGCCAGCGCCCTAGCGCCCGCTCCTTTCGCTTTC
TTCCCTTCCTTTCTCGCGACGTTCGCCGGCTTTCCCCGTCAAGCTCTAAA
TCGGGGGCTCCCTTTAGGGTTCCGATTTAGTGCTTTACGGCACCTCGACC
CCAAAAAACTTGATTAGGGTGATGGTTCACGTAGTGGGCCATCGCCCTGA
TAGACGGTTTTTCGCCCTTTGACGTTGGAGTCCACGTTCTTTAATAGTGG
ACTCTTGTTCCAAACTGGAACAACACTCAAGCCTATCTCGGTCTATTCTT
TTGATTTATAAGGGATTTTGCCGATTTCGGCCTATTGGTTAAAAAATGAG
CTGATTTAACAAAAATTTAACGCGAATTTTAACAAAATATTAACGTTTAC
AATTTAAATATTTGCTTATACAATCTTCCTGTTTTTGGGGCTTTTCTGAT
TATCAACCGGGGTACATATGATTGACATGCTAGTTTTACGATTACCGTTC
ATCGATTCTCTTGTTTGCTCCAGACTCTCAGGCAATGACCTGATAGCCTT
TGTAGAGACCTCTCAAAAATAGCTACCCTCTCCGGCATGAATTTATCAGC
TAGAACGGTTGAATATCATATTGATGGTGATTTGACTGTCTCCGGCCTTT
CTCACCCGTTTGAATCTTTACCTACACATTACTCAGGCATTGCATTTAAA
ATATATGAGGGTTCTAAAAATTTTTATCCTTGCGTTGAAATAAAGGCTTC
TCCCGCAAAAGTATTACAGGGTCATAATGTTTTTGGTACAACCGATTTAG
CTTTATGCTCTGAGGCTTTATTGCTTAATTTTGCTAATTCTTTGCCTTGC
CTGTATGATTTATTGGATGTTGCAATTCCTGATGCGGTATTTTCTCCTTA
CGCATCTGTGCGGTATTTCACACCGCATATGGTGCACTCTCAGTACAATC
TGCTCTGATGCCGCATAGTTAAGCCAGCCCCGACACCCGCCAACACCCGC
TGACGCGCCCTGACGGGCTTGTCTGCTCCCGGCATCCGCTTACAGACAAG
CTGTGACCGTCTCCGGGAGCTGCATGTGTCAGAGGTTTTCACCGTCATCA
CCGAAACGCGCGAGACGAAAGGGCCTCGTGATACGCCTATTTTTATAGGT
TAATGTCATGATAATAATGGTTTCTTAGACGTCAGGTGGCACTTTTCGGG
GAAATGTGCGCGGAACCCCTATTTGTTTATTTTTCTAAATACATTCAAAT
ATGTATCCGCTCATGAGACAATAACCCTGATAAATGCTTCAATAATATTG
AAAAAGGAAGAGTATGAGTATTCAACATTTCCGTGTCGCCCTTATTCCCT
TTTTTGCGGCATTTTGCCTTCCTGTTTTTGCTCACCCAGAAACGCTGGTG
AAAGTAAAAGATGCTGAAGATCAGTTGGGTGCACGAGTGGGTTACATCGA
ACTGGATCTCAACAGCGGTAAGATCCTTGAGAGTTTTCGCCCCGAAGAAC
GTTTTCCAATGATGAGCACTTTTAAAGTTCTGCTATGTGGCGCGGTATTA
TCCCGTATTGACGCCGGGCAAGAGCAACTCGGTCGCCGCATACACTATTC
TCAGAATGACTTGGTTGAGTACTCACCAGTCACAGAAAAGCATCTTACGG
ATGGCATGACAGTAAGAGAATTATGCAGTGCTGCCATAACCATGAGTGAT
AACACTGCGGCCAACTTACTTCTGACAACGATCGGAGGACCGAAGGAGCT
AACCGCTTTTTTGCACAACATGGGGGATCATGTAACTCGCCTTGATCGTT
```

```
GGGAACCGGAGCTGAATGAAGCCATACCAAACGACGAGCGTGACACCACG
ATGCCTGTAGCAATGGCAACAACGTTGCGCAAACTATTAACTGGCGAACT
ACTTACTCTAGCTTCCCGGCAACAATTAATAGACTGGATGGAGGCGGATA
AAGTTGCAGGACCACTTCTGCGCTCGGCCCTTCCGGCTGGCTGGTTTATT
GCTGATAAATCTGGAGCCGGTGAGCGTGGGTCTCGCGGTATCATTGCAGC
ACTGGGGCCAGATGGTAAGCCCTCCCGTATCGTAGTTATCTACACGACGG
GGAGTCAGGCAACTATGGATGAACGAAATAGACAGATCGCTGAGATAGGT
GCCTCACTGATTAAGCATTGGTAACTGTCAGACCAAGTTTACTCATATAT
ACTTTAGATTGATTTAAAACTTCATTTTTAATTTAAAAGGATCTAGGTGA
AGATCCTTTTTGATAATCTCATGACCAAAATCCCTTAACGTGAGTTTTCG
TTCCACTGAGCGTCAGACCCCGTAGAAAAGATCAAAGGATCTTCTTGAGA
TCCTTTTTTTCTGCGCGTAATCTGCTGCTTGCAAACAAAAAAACCACCGC
TACCAGCGGTGGTTTGTTTGCCGGATCAAGAGCTACCAACTCTTTTTCCG
AAGGTAACTGGCTTCAGCAGAGCGCAGATACCAAATACTGTCCTTCTAGT
GTAGCCGTAGTTAGGCCACCACTTCAAGAACTCTGTAGCACCGCCTACAT
ACCTCGCTCTGCTAATCCTGTTACCAGTGGCTGCTGCCAGTGGCGATAAG
TCGTGTCTTACCGGGTTGGACTCAAGACGATAGTTACCGGATAAGGCGCA
GCGGTCGGGCTGAACGGGGGGTTCGTGCACACAGCCCAGCTTGGAGCGAA
CGACCTACACCGAACTGAGATACCTACAGCGTGAGCTATGAGAAAGCGCC
ACGCTTCCCGAAGGGAGAAAGGCGGACAGGTATCCGGTAAGCGGCAGGGT
CGGAACAGGAGAGCGCACGAGGGAGCTTCCAGGGGGAAACGCCTGGTATC
TTTATAGTCCTGTCGGGTTTCGCCACCTCTGACTTGAGCGTCGATTTTTG
TGATGCTCGTCAGGGGGCGGAGCGTATGGAAAAACGCCAGCAACGCGGG
CTTTTTACGGTTCCTGGCCTTTTGCTGGCCTTTTGCTCACATGTTCTTTC
CTGCGTTATCCCCTGATTCTGTGGATAACCGTATTACCGCCTTTGAGTGA
GCTGATACCGCTCGCCGGAGCCGAACGACCGAGCGCAGCGAGTCAGTGAG
CGAGGAAGCGGAAGAGCGCCCAATACGCAAAC
```

SEQ ID NO: 2. Complete sequence of packing plasmid pXX2 with the bone-tag sequence (pXX2-ND8-8.4 kb). Initial codon for capsid proteins VP1, VP2 and VP3 are shown in bold. Sequence encoding for the amino acidic octapeptide is underlined.

```
CGCCTCTCCCCGCGCGTTGGCCGATTCATTAATGCAGAATTCCCATCATC
AATAATATACCTTATTTTGGATTGAAGCCAATATGATAATGAGGGGTGG
AGTTTGTGACGTGGCGCGGGGCGTGGGAACGGGCGGGTGACGTAGTAGC
TCTAGAGGTCCTGTATTAGAGGTCACGTGAGTGTTTTGCGACATTTTGCG
ACACCATGTGGTCACGCTGGGTATTTAAGCCCGAGTGAGCACGCAGGGTC
TCCATTTTGAAGCGGGAGGTTTGAACGCGCAGCCACCACGGCGGGGTTTT
ACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCC
GCCAGATTCTGACATGGATCTGAATCTGATTGAGCAGGCACCCCTGACCG
```

TGGCCGAGAAGCTGCAGCGCGACTTTCTGACGGAATGGCGCCGTGTGAGT
AAGGCCCCGGAGGCCCTTTTCTTTGTGCAATTTGAGAAGGGAGAGAGCTA
CTTCCACATGCACGTGCTCGTGGAAACCACCGGGGTGAAATCCATGGTTT
TGGGACGTTTCCTGAGTCAGATTCGCGAAAAACTGATTCAGAGAATTTAC
CGCGGGATCGAGCCGACTTTGCCAAACTGGTTCGCGGTCACAAAGACCAG
AAATGGCGCCGGAGGCGGGAACAAGGTGGTGGATGAGTGCTACATCCCCA
ATTACTTGCTCCCCAAAACCCAGCCTGAGCTCCAGTGGGCGTGGACTAAT
ATGGAACAGTATTTAAGCGCCTGTTTGAATCTCACGGAGCGTAAACGGTT
GGTGGCGCAGCATCTGACGCACGTGTCGCAGACGCAGGAGCAGAACAAAG
AGAATCAGAATCCCAATTCTGATGCGCCGGTGATCAGATCAAAAACTTCA
GCCAGGTACATGGAGCTGGTCGGGTGGCTCGTGGACAAGGGGATTACCTC
GGAGAAGCAGTGGATCCAGGAGGACCAGGCCTCATACATCTCCTTCAATG
CGGCCTCCAACTCGCGGTCCCAAATCAAGGCTGCCTTGGACAATGCGGGA
AAGATTATGAGCCTGACTAAAACCGCCCCGACTACCTGGTGGGCCAGCA
GCCCGTGGAGGACATTTCCAGCAATCGGATTTATAAAATTTTGGAACTAA
ACGGGTACGATCCCCAATATGCGGCTTCCGTCTTTCTGGGATGGGCCACG
AAAAAGTTCGGCAAGAGGAACACCATCTGGCTGTTTGGGCCTGCAACTAC
CGGGAAGACCAACATCGCGGAGGCCATAGCCCACACTGTGCCCTTCTACG
GGTGCGTAAACTGGACCAATGAGAACTTTCCCTTCAACGACTGTGTCGAC
AAGATGGTGATCTGGTGGGAGGAGGGGAAGATGACCGCCAAGGTCGTGGA
GTCGGCCAAAGCCATTCTCGGAGGAAGCAAGGTGCGCGTGGACCAGAAAT
GCAAGTCCTCGGCCCAGATAGACCCGACTCCCGTGATCGTCACCTCCAAC
ACCAACATGTGCGCCGTGATTGACGGGAACTCAACGACCTTCGAACACCA
GCAGCCGTTGCAAGACCGGATGTTCAAATTTGAACTCACCCGCCGTCTGG
ATCATGACTTTGGGAAGGTCACCAAGCAGGAAGTCAAAGACTTTTTCCGG
TGGGCAAAGGATCACGTGGTTGAGGTGGAGCATGAATTCTACGTCAAAAA
GGGTGGAGCCAAGAAAAGACCCGCCCCCAGTGACGCAGATATAAGTGAGC
CCAAACGGGTGCGCGAGTCAGTTGCGCAGCCATCGACGTCAGACGCGGAA
GCTTCGATCAACTACGCAGACAGGTACCAAAACAAATGTTCTCGTCACGT
GGGCATGAATCTGATGCTGTTTCCCTGCAGACAATGCGAGAGAATGAATC
AGAATTCAAATATCTGCTTCACTCACGGACAGAAAGACTGTTTAGAGTGC
TTTCCCGTGTCAGAATCTCAACCCGTTTCTGTCGTCAAAAAGGCGTATCA
GAAACTGTGCTACATTCATCATATCATGGGAAAGGTGCCAGACGCTTGCA
CTGCCTGCGATCTGGTCAATGTGGATTTGGATGACTGCATCTTTGAACAA
TAAATGATTTAAATCAGGTATGGCTGCCGATGGTTATCTTCCAGATTGGC
TCGAGGACAGTCTCTCTGAAGGAATAAGACAGTGGTGGAAGCTCAAACCT
GGCCCACCACCACCAAAGCCCGCAGAGCGGCATAAGGACGACAGCAGGGG
TCTTGTGCTTCCTGGGTACAAGTACCTCGGACCCTTCAACGGACTCGACA
AGGGAGAGCCGGTCAACGAGGCAGACGCCGCGGCCCTCGAGCACGACAAA
GCCTACGACCGGCAGCTCGACAGCGGAGACAACCCGTACCTCAAGTACAA

CCACGCCGACGCGGAGTTTCAGGAGCGCCTTAAAGAAGATACGTCTTTTG
GGGGCAACCTCGGACGAGCAGTCTTCCAGGCGAAAAAGAGGGTTCTTGAA
CCTCTGGGCCTGGTTGAGGAACCTGTTAAGACG<u>GATGATGATGATGATGA
TGACGAC</u>GCTCCGGGAAAAAGAGGCCGGTAGAGCACTCTCCTGTGGAGC
CAGACTCCTCCTCGGGAACCGGAAAGGCGGGCCAGCAGCCTGCAAGAAAA
AGATTGAATTTTGGTCAGACTGGAGACGCAGACTCAGTACCTGACCCCCA
GCCTCTCGGACAGCCACCAGCAGCCCCCTCTGGTCTGGGAACTAATACGA
TGGCTACAGGCAGTGGCGCACCAATGGCAGACAATAACGAGGGCGCCGAC
GGAGTGGGTAATTCCTCGGGAAATTGGCATTGCGATTCCACATGGATGGG
CGACAGAGTCATCACCACCAGCACCCGAACCTGGGCCCTGCCCACCTACA
ACAACCACCTCTACAAACAAATTTCCAGCCAATCAGGAGCCTCGAACGAC
AATCACTACTTTGGCTACAGCACCCCTTGGGGGTATTTTGACTTCAACAG
ATTCCACTGCCACTTTTCACCACGTGACTGGCAAAGACTCATCAACAACA
ACTGGGGATTCCGACCCAAGAGACTCAACTTCAAGCTCTTTAACATTCAA
GTCAAAGAGGTCACGCAGAATGACGGTACGACGACGATTGCCAATAACCT
TACCAGCACGGTTCAGGTGTTTACTGACTCGGAGTACCAGCTCCCGTACG
TCCTCGGCTCGGCGCATCAAGGATGCCTCCCGCCGTTCCCAGCAGACGTC
TTCATGGTGCCACAGTATGGATACCTCACCCTGAACAACGGGAGTCAGGC
AGTAGGACGCTCTTCATTTTACTGCCTGGAGTACTTTCCTTCTCAGATGC
TGCGTACCGGAAACAACTTTACCTTCAGCTACACTTTTGAGGACGTTCCT
TTCCACAGCAGCTACGCTCACAGCCAGAGTCTGGACCGTCTCATGAATCC
TCTCATCGACCAGTACCTGTATTACTTGAGCAGAACAAACACTCCAAGTG
GAACCACCACGCAGTCAAGGCTTCAGTTTTCTCAGGCCGGAGCGAGTGAC
ATTCGGGACCAGTCTAGGAACTGGCTTCCTGGACCCTGTTACCGCCAGCA
GCGAGTATCAAAGACATCTGCGGATAACAACAACAGTGAATACTCGTGGA
CTGGAGCTACCAAGTACCACCTCAATGGCAGAGACTCTCTGGTGAATCGG
GGCCCGGCCATGGCAAGCCACAAGGACGATGAAGAAAAGTTTTTTCCTCA
GAGCGGGGTTCTCATCTTTGGGAAGCAAGGCTCAGAGAAAACAAATGTGG
ACATTGAAAAGGTCATGATTACAGACGAAGAGGAAATCAGGACAACCAAT
CCCGTGGCTACGGAGCAGTATGGTTCTGTATCTACCAACCTCCAGAGAGG
CAACAGACAAGCAGCTACCGCAGATGTCAACACACAAGGCGTTCTTCCAG
GCATGGTCTGGCAGGAGAGAGATGTGTACCTTCAGGGGCCCATCTGGGCA
AAGATTGCACACACGGACGGACATTTTCACCCCTCTCCCCTCATGGGTGG
ATTCGGACTTAAACACCCTCCTCCACAGATTCTCATCAAGAACACCCCGG
TACCTGCGAATCCTTCGACCACCTTCAGTGCGGCAAAGTTTGCTTCCTTC
ATCACACAGTACTCCACGGGACAGGTCAGCGTGGAGATCGAGTGGGAGCT
GCAGAAGGAAAACAGCAAACGCTGGAATCCCGAAATTCAGTACACTTCCA
ACTACAACAAGTCTGTTAATGTGGACTTTACTGTGGACACTAATGGCGTG
TATTCAGAGCCTCGCCCCATTGGCACCAGATACCTGACTCGTAATCTGTA
ATTGCTTGTTAATCAATAAACCGTTTAATTCGTTTCAGTTGAACTTTGGT
CTCTGCGTATTTCTTTCTTATCTAGTTTCCATGCTCTAGAGGGTCCTGTAT

```
TAGAGGTCACGTGAGTGTTTTGCGACATTTTGCGACACCATGTGGTCACG
CTGGGTATTTAAGCCCGAGTGAGCACGCAGGGTCTCCATTTTGAAGCGGG
AGGTTTGAACGCGCAGCCACCACGGCGGGGTTTTACGAGATTGTGATTAA
GGTCCCCAGCGACCTTGACGAGCATCTGCCCGGCATTTCTGACAGCTTTG
TGAACTGGGTGGCCGAGAAGGAATGGGAGTTGCCGCCAGATTCTGACATG
GATCTGAATCTGATTGAGCAGGCACCCCTGACCGTGGCCGAGAAGCTGCA
TCGCTGGCGTAATAGCGAAGAGGCCCGCACCGATCGCCCTTCCCAACAGT
TGCGCAGCCTGAATGGCGAATGGCGATTCCGTTGCAATGGCTGGCGGTAA
TATTGTTCTGGATATTACCAGCAAGGCCGATAGTTTGAGTTCTTCTACTC
AGGCAAGTGATGTTATTACTAATCAAAGAAGTATTGCGACAACGGTTAAT
TTGCGTGATGGACAGACTCTTTTACTCGGTGGCCTCACTGATTATAAAAA
CACTTCTCAGGATTCTGGCGTACCGTTCCTGTCTAAAATCCCTTTAATCG
GCCTCCTGTTTAGCTCCCGCTCTGATTCTAACGAGGAAAGCACGTTATAC
GTGCTCGTCAAAGCAACCATAGTACGCGCCCTGTAGCGGCGCATTAAGCG
CGGCGGGTGTGGTGGTTACGCGCAGCGTGACCGCTACACTTGCCAGCGCC
CTAGCGCCCGCTCCTTTCGCTTTCTTCCCTTCCTTTCTCGCCACGTTCGC
CGGCTTTCCCCGTCAAGCTCTAAATCGGGGCTCCCTTTAGGGTTCCGAT
TTAGTGCTTTACGGCACCTCGACCCCAAAAAACTTGATTAGGGTGATGGT
TCACGTAGTGGGCCATCGCCCTGATAGACGGTTTTTCGCCCTTTGACGTT
GGAGTCCACGTTCTTTAATAGTGGACTCTTGTTCCAAACTGGAACAACAC
TCAACCCTATCTCGGTCTATTCTTTTGATTTATAAGGGATTTTGCCGATT
TCGGCCTATTGGTTAAAAAATGAGCTGATTTAACAAAAATTTAACGCGAA
TTTTAACAAAATATTAACGTTTACAATTTAAATATTTGCTTATACAATCT
TCCTGTTTTTGGGGCTTTTCTGATTATCAACCGGGGTACATATGATTGAC
ATGCTAGTTTTACGATTACCGTTCATCGATTCTCTTGTTTGCTCCAGACT
CTCAGGCAATGACCTGATAGCCTTTGTAGAGACCTCTCAAAAATAGCTAC
CCTCTCCGGCATGAATTTATCAGCTAGAACGGTTGAATATCATATTGATG
GTGATTTGACTGTCTCCGGCCTTTCTCACCCGTTTGAATCTTTACCTACA
CATTACTCAGGCATTGCATTTAAAATATATGAGGGTTCTAAAAATTTTTA
TCCTTGCGTTGAAATAAAGGCTTCTCCCGCAAAAGTATTACAGGGTCATA
ATGTTTTTGGTACAACCGATTTAGCTTTATGCTCTGAGGCTTTATTGCTT
AATTTTGCTAATTCTTTGCCTTGCCTGTATGATTTATTGGATGTTGCAAT
TCCTGATGCGGTATTTTCTCCTTACGCATCTGTGCGGTATTTCACACCGC
ATATGGTGCACTCTCAGTACAATCTGCTCTGATGCCGCATAGTTAAGCCA
GCCCCGACACCCGCCAACACCCGCTGACGCGCCCTGACGGGCTTGTCTGC
TCCCGGCATCCGCTTACAGACAAGCTGTGACCGTCTCCGGGAGCTGCATG
TGTCAGAGGTTTTCACCGTCATCACCGAAACGCGCGAGACGAAAGGGCCT
CGTGATACGCCTATTTTTATAGGTTAATGTCATGATAATAATGGTTTCTT
AGACGTCAGGTGGCACTTTTCGGGGAAATGTGCGCGGAACCCCTATTTGT
```

```
TTATTTTTCTAAATACATTCAAATATGTATCCGCTCATGAGACAATAACC
CTGATAAATGCTTCAATAATATTGAAAAAGGAAGAGTATGAGTATTCAAC
ATTTCCGTGTCGCCCTTATTCCCTTTTTTGCGGCATTTTGCCTTCCTGTT
TTTGCTCACCCAGAAACGCTGGTGAAAGTAAAAGATGCTGAAGATCAGTT
GGGTGCACGAGTGGGTTACATCGAACTGGATCTCAACAGCGGTAAGATCC
TTGAGAGTTTTCGCCCCGAAGAACGTTTTCCAATGATGAGCACTTTTAAA
GTTCTGCTATGTGGCGCGGTATTATCCCGTATTGACGCCGGGCAAGAGCA
ACTCGGTCGCCGCATACACTATTCTCAGAATGACTTGGTTGAGTACTCAC
CAGTCACAGAAAAGCATCTTACGGATGGCATGACAGTAAGAGAATTATGC
AGTGCTGCCATAACCATGAGTGATAACACTGCGGCCAACTTACTTCTGAC
AACGATCGGAGGACCGAAGGAGCTAACCGCTTTTTTGCACAACATGGGGG
ATCATGTAACTCGCCTTGATCGTTGGGAACCGGAGCTGAATGAAGCCATA
CCAAACGACGAGCGTGACACCACGATGCCTGTAGCAATGGCAACAACGTT
GCGCAAACTATTAACTGGCGAACTACTTACTCTAGCTTCCCGGCAACAAT
TAATAGACTGGATGGAGGCGGATAAAGTTGCAGGACCACTTCTGCGCTCG
GCCCTTCCGGCTGGCTGGTTTATTGCTGATAAATCTGGAGCCGGTGAGCG
TGGGTCTCGCGGTATCATTGCAGCACTGGGGCCAGATGGTAAGCCCTCCC
GTATCGTAGTTATCTACACGACGGGGAGTCAGGCAACTATGGATGAACGA
AATAGACAGATCGCTGAGATAGGTGCCTCACTGATTAAGCATTGGTAACT
GTCAGACCAAGTTTACTCATATATACTTTAGATTGATTTAAAACTTCATT
TTTAATTTAAAAGGATCTAGGTGAAGATCCTTTTTGATAATCTCATGACC
AAAATCCCTTAACGTGAGTTTTCGTTCCACTGAGCGTCAGACCCCGTAGA
AAAGATCAAAGGATCTTCTTGAGATCCTTTTTTTCTGCGCGTAATCTGCT
GCTTGCAAACAAAAAAACCACCGCTACCAGCGGTGGTTTGTTTGCCGGAT
CAAGAGCTACCAACTCTTTTTCCGAAGGTAACTGGCTTCAGCAGAGCGCA
GATACCAAATACTGTCCTTCTAGTGTAGCCGTAGTTAGGCCACCACTTCA
AGAACTCTGTAGCACCGCCTACATACCTCGCTCTGCTAATCCTGTTACCA
GTGGCTGCTGCCAGTGGCGATAAGTCGTGTCTTACCGGGTTGGACTCAAG
ACGATAGTTACCGGATAAGGCGCAGCGGTCGGGCTGAACGGGGGGTTCGT
GCACACAGCCCAGCTTGGAGCGAACGACCTACACCGAACTGAGATACCTA
CAGCGTGAGCTATGAGAAAGCGCCACGCTTCCCGAAGGGAGAAAGGCGGA
CAGGTATCCGGTAAGCGGCAGGGTCGGAACAGGAGAGCGCACGAGGGAGC
TTCCAGGGGGAAACGCCTGGTATCTTTATAGTCCTGTCGGGTTTCGCCAC
CTCTGACTTGAGCGTCGATTTTTGTGATGCTCGTCAGGGGGCGGAGCCT
ATGGAAAAACGCCAGCAACGCGGCCTTTTTACGGTTCCTGGCCTTTTGCT
GGCCTTTTGCTCACATGTTCTTTCCTGCGTTATCCCCTGATTCTGTGGAT
AACCGTATTACCGCCTTTGAGTGAGCTGATACCGCTCGCCGCAGCCGAAC
GACCGAGCGCAGCGAGTCAGTGAGCGAGGAAGCGGAAGAGCGCCCAATAC
GCAAAC
```

What is claimed is:

1. An insolated adeno-associated virus, comprising a capsid encoded by SEQ ID NO: 2, and capable of transfecting single stranded DNA into a mammalian cell.

2. The composition of claim 1, further comprises a physiological composition suitable for administration to a subject in need.

3. The composition of claim 1, wherein the adeno-associated virus comprises a single stranded DNA encoding N-acetylgalactosamine-6-sulfate-sulfatase, whereby the single stranded DNA expresses a physiologically active N-acetylgalactosamine-6-sulfate-sulfatase after transfection into a mammalian cell.

4. The composition of claim 3, wherein the N-acetylgalactosamine-6-sulfate-sulfatase is wild type.

5. An insolated adeno-associated virus, comprising,
a) a capsid encoded by SEQ ID NO: 2;
b) single stranded DNA encoding wild type N-acetylgalactosamine-6-sulfate-sulfatase;
c) whereby the adeno-associated virus targets bone in vivo; and
d) whereby a physiologically active wild type N-acetylgalactosamine-6-sulfate-sulfatase is expressed after transfection of the adeno-associated virus into a mammalian cell.

* * * * *